US012508189B1

(12) United States Patent
Turner

(10) Patent No.: US 12,508,189 B1
(45) Date of Patent: Dec. 30, 2025

(54) METHODS AND APPARATUS FOR TREATING PAIN AND MOBILITY IMPAIRMENT

(71) Applicant: David G. Turner, Livermore, CA (US)

(72) Inventor: David G. Turner, Livermore, CA (US)

( * ) Notice: Subject to any disclaimer, the term of this patent is extended or adjusted under 35 U.S.C. 154(b) by 676 days.

(21) Appl. No.: 17/407,095

(22) Filed: Aug. 19, 2021

Related U.S. Application Data

(60) Provisional application No. 63/067,325, filed on Aug. 19, 2020.

(51) Int. Cl.

| | |
|---|---|
| ***A61H 9/00*** | (2006.01) |
| ***A61N 1/36*** | (2006.01) |
| ***A61N 1/362*** | (2006.01) |

(52) U.S. Cl.

CPC ......... *A61H 9/0057* (2013.01); *A61N 1/3621* (2013.01); *A61H 2009/0064* (2013.01); *A61H 2201/10* (2013.01); *A61H 2201/5071* (2013.01); *A61H 2201/5082* (2013.01); *A61H 2201/5092* (2013.01)

(58) Field of Classification Search

CPC .......... A61H 9/0057; A61H 2009/0064; A61H 2201/10; A61H 2201/5071; A61H 2201/5082; A61H 2201/5092; A61H 7/00; A61H 7/001; A61H 7/008; A61H 39/002; A61H 9/00; A61H 9/005; A61H 2201/013; A61H 2201/0153; A61H 2201/0157; A61H 2201/1238; A61H 2201/1409; A61H 2201/168; A61H 2201/5007; A61H 2201/5085; A61H 2230/50; A61H 2230/505; A61H 2230/85; A61H 2230/855; A61H 23/04; A61N 1/36021

USPC ............................................................. 601/6

See application file for complete search history.

(56) References Cited

U.S. PATENT DOCUMENTS 6,030,318 A * 2/2000 Howard ................. A61H 9/005 482/4
6,277,052 B1 * 8/2001 Howard ................. A61H 19/32 482/4
6,328,709 B1 * 12/2001 Hung ..................... A61B 5/444 604/74
7,229,422 B2 * 6/2007 Klobe ....................... A61F 5/01 601/6
9,295,607 B2 * 3/2016 Rosenberg ............. A61H 7/003

(Continued)

FOREIGN PATENT DOCUMENTS

CN 200998397 Y * 1/2008
CN 101537212 A * 9/2009

(Continued)

*Primary Examiner* — Tu A Vo
*Assistant Examiner* — Kelsey E Baller
(74) *Attorney, Agent, or Firm* — Daniel L. Flamm; Microtechnology Law & Analysis

(57) ABSTRACT

Methods and apparatus disclosed for treating pain and mobility impairments include synergistic application of various stimuli to a patient. These stimuli can comprise serial and sequential combinations of predetermined subatmospheric pressure values, time-varying voltage waveforms applied to electrodes in contact with different portions of a patient's skin in a matter that produces currents which stimulate nerve fibers that activate muscles, and direct practitioner-assisted mechanical movement of tissue. Apparatus and systems for applying the treatment methods are disclosed.

1 Claim, 12 Drawing Sheets

(56) References Cited

U.S. PATENT DOCUMENTS

2002/0002346 A1* 1/2002 Horst .................... A61H 9/005 601/6
2003/0125646 A1* 7/2003 Whitlock ............... A61H 9/005 601/6
2006/0206040 A1* 9/2006 Greenberg ............. A61H 9/005 601/7
2007/0208281 A1* 9/2007 Brooks ................... A61M 1/08 601/6
2008/0015474 A1* 1/2008 Quinn .................... A61H 9/005 601/6
2012/0215142 A1* 8/2012 Spector .............. A61B 17/2251 601/46
2014/0163437 A1* 6/2014 Mack ..................... A61H 19/40 601/46
2014/0336543 A1* 11/2014 Idowu .................. A61H 9/0057 601/6
2015/0231021 A1* 8/2015 Smith ................... A61M 27/00 601/7
2015/0313788 A1* 11/2015 Conte .................. A61H 9/0057 601/6
2016/0022530 A1* 1/2016 Saló Darder ........ A61H 9/0057 601/6
2016/0128894 A1* 5/2016 Horton ................... A61B 18/12 601/11
2016/0206790 A1* 7/2016 Weston ............. A61F 13/00068
2017/0196756 A1* 7/2017 Palomäki ............. A61H 9/0057
2017/0290732 A1* 10/2017 Palomäki ............... A61H 9/005
2018/0214618 A1* 8/2018 Mostafa .................. A61M 1/08
2018/0325772 A1* 11/2018 Liu ........................ A61H 39/06
2019/0029917 A1* 1/2019 George ................ A61H 9/0007
2020/0282212 A1* 9/2020 Busoni ..................... A61N 1/40
2021/0038466 A1* 2/2021 Stewart, Jr. .......... A61N 1/0472
2021/0228876 A1* 7/2021 Mason ................. A61N 1/0404

FOREIGN PATENT DOCUMENTS

JP 2006289098 A * 10/2006 ........... A61B 17/205
WO WO-2012089910 A1 * 7/2012 ............. A61H 23/00

* cited by examiner

METHODS AND APPARATUS FOR TREATING PAIN AND MOBILITY IMPAIRMENT

CROSS-REFERENCES TO RELATED APPLICATIONS

This present application claims the benefit of U.S. Provisional Application No. 63/067,335 filed on Aug. 19, 2020.

FIELD OF THE INVENTION

The present disclosure relates generally to the art of alleviating human movement impairments and pain caused by injury, stress or a lack of activity, and more particularly relates to soft tissue reconfiguration therapy to modify the plasticity and shape of soft tissue to improve the recovery of injured tissues or maintain overall fitness and strength.

BACKGROUND

Impaired movement and pain are common health problems. According to the Center of Disease Control, it affects about 14% of adults in the USA. Among people with the age of 65 years old and older, it increases even further to 40%. Similarly, pain is also a common problem. Almost 90% of people experience a least one kind of tissue induced pain during their life. Common causes of movement impairments include soft tissue injuries and various diseases, which manifest in muscles, neurons or other types of tissue implicated in body movements, movement regulation and coordination, and aging. Myofascial pain is one of the most common types of chronic pain which can be triggered by pressure sensitive regions in muscles and connective tissues. Myofascial pain can also lead to muscle weakness and movement limitations. About 30% to 85% of patients with pain are reported to suffer myofascial pain ("Prevalence of myofascial pain in general internal medicine practice" S. A. Skootsky, B. Jaeger, and R K Oye, West J. Med. 1989 August, 151 (2): 157-160, all of which are hereby incorporated by reference in their entirety). These health problems not only decrease the quality of a patient's life and independence, and the patient's ability to perform daily activities, but also cause significant economic burden to society owing to loss of productivity and cost of care. Despite the high prevalence of movement impairments and pain, they are commonly untreated and/or undertreated.

Cupping therapy is a soft tissue decompression treatment generally performed by applying negative pressure to an area of skin 1020 using a cup 1010 (shown in FIG. 1). Cupping is known to enhance recovery from certain types of injuries. Various methods of cupping therapy were practiced in ancient Egypt, China, and the New World for millennia. Cups 1010 are positioned on the skin 1020 of a patient, sometimes at predetermined locations, and a vacuum is applied to the skin positions by evacuating air through an aperture in each cup. As seen in FIGS. 2A, 2B, 2C, the negative pressure causes soft tissue in its initial configuration seen in FIG. 2A to be extruded into the vacuum within a cup (FIG. 2B). Typically, some distension persists for a time after removal of the cup FIG. 2C. Some practitioners of Asian folk medicine apparently believed cupping therapy modifies and ameliorates a flow of energy and/or imbalances causing and/or arising from injuries and diseases. The cupping is also referred to as myofascial decompression (MFD). Some contemporary cupping practitioners teach cupping therapy augmented by movements can alleviate and/or remediate some mobility impairments by inducing the body to reconfigure connective tissue and its interactions with the neuromuscular and musculoskeletal systems.

Elements of connective tissue in the human body are generally known as "fascia". The fasciae, which are present throughout the body, provide supporting structure and protective tissue for muscles, bones and other structural supporting elements including those which coordinate and enable mobility. The structure and functions of fasciae vary with position in the body.

FIG. 3 shows the skin 1020 and various underlying layers of soft tissue. The superficial fascia layer 3030 can be in the form of dense fibrous sheets and bands immediately below the skin 1020. Superficial fascia can comprise areolar and adipose tissue which can protect deeper underlying tissue and facilitate mobility. The superficial fascia layer 3030 extends to a deep fascia layer 3040. The deep fascia 3040 provides structural support that facilitates movement of muscle below 3060.

Fascia comprise three main components: collagen and elastin fibers, extracellular matrix proteins (termed "ground substance"), and various cell types including fibroblast, adipocytes, and macrophages, mast cells and leucocytes. The collagen and elastin fibers provide tensile strength and elasticity to fascia and surrounding structure, and facilitate the sliding of layers over one another and stretching. Ground substance is a viscoelastic material that fills space between cells and fibers consisting of mainly various proteoglycans and polysaccharides.

Proteoglycans can reversibly bind to an hyaluronic acid HA "backbone" forming large protein polysaccharide complexes. The number of proteoglycans attached to the HA backbone (determined by the local water and ion content, pH, and temperature) determines the fluidity and viscosity characteristics of the ground substance. A lower viscosity (higher tissue fluidity) results in less friction between fiber layers and relatively greater mobility. The fibroblast secretes collagen and other components of the ground substance. Adipocytes store fat. Macrophages, mast cells and leucocytes are involved in tissue inflammation. These various cells act cooperatively in tissue regeneration and wound healing after injuries and/or other types of tissue impairments.

Injuries, diseases, trauma, prolonged intense activity, and/or inactivity can provoke muscle and fascia pain (myofascial pain). Myofascial pain can involve muscle, sensory and motor neurons, and/or the autonomic nervous system. Myofascial pain is often gated in the neighborhood of myofascial trigger points (MTPs) and/or facial restriction. FIG. 4 shows a number of common trigger point locations including masseter 1, pectoralis minor 2, pectoralis major 3, bicep 4, deltoid 5, flexor carpi radialis 6, flexor carpi ulnaris 7, flexor pollicis brevis 8, rectus abdominus 9, tensor fascia lata 10, vastus lateralis 11, vastus intermedius 12, vastus medialis 13, extensor digitorum 14, peroneal 15, posterior tibialis 16, levator scapulae 17, infraspinatus 18, rhomboid 19, triceps 20, extensor carpi radialis 21, extensor digitorum 22, lumbar paraspinal/multifidus 23, gluteus medius 24, piriformis 25, bicep femoris 26, semitendinosus 27, gastroc 29, soleus 29, and capitis 30. Characteristically, MTPs are hyperirritable tender spots within the taut bands of skeletal muscles that form palpable nodules (see "Myofascial Pain and Dysfunction The Trigger Point Manual The Lower Extremities" (Volume 2) J. G. Travell and D. G. Simons, Lippincott Williams and Wilkins 1983 which is hereby incorporated by reference in its entirety for all purposes). Taut bands are groups of tense muscle fibers that have shortened and/or lengthened muscle fiber units known as sarcomeres. Touching one of the trigger points can induce localized pain at the trigger point, and/or pain at other locations (also called "referred pain"), and can activate transient asynchronous contractions of taut bands in muscle fibers (known as a "local twitch response"). These MTPs are generally assessed by evaluating relative tenderness, taut band characteristics and the degree of painfulness. A trigger point can activate both sensory and motor components.

Trigger points can be in a latent or in an active state. Latent trigger points are usually tender but do not manifest pain. Active trigger points, on the other hand, can be tender and painful with or without movement. A trigger point can change from being latent to active, or the reverse, and a sensation originating at a trigger point can travel to a remote location.

By comparison with normal healthy tissue, tissue surrounding a trigger point generally has less blood flow (known as "ischemia") and reduced levels of nutrients and oxygen (also known as hypoxia). As such, these tissues exhibit diminished energy release. At trigger points, there are relatively higher levels of calcium in muscles which cause a shortening of sarcomeres in the skeletal muscles involved in initiating voluntary movements as well as involuntary chronic muscle fiber contractions and/or spasms. The imposition of mechanical stress (force per cross sectional area of the tissue) to trigger points can provoke pain by activating pain receptors (termed as "nociceptors") in sensory neurons, muscles, skin, joints, and visceral organs, and can cause abnormal pain stimulus from sensory neurons to be sent to the spinal cord and brain. Thus, mechanical stress can induce the perception of pain in various degrees.

In another aspect, injury, inactivity or excess repetitive activity may induce dehydration in fascia. Such dehydration is known to stimulate production of "sticky" inelastic macromolecules that can impede normal movement and reduce soft tissue elasticity. This typically reduces the operable range of muscle kinematics and movement of neighboring joints. These adhesions can also increase neuromuscular hypertonicity resulting in reduced strength, endurance, and muscle coordination in affected individuals.

Fasciae have the ability to switch back and forth from a gel-like state to liquid-like state depending upon application of shear force and local micro-environment parameters such as temperature, pH, ionic conditions etc., evidently because of the "thixotropic" nature of the ground substance. High temperatures (up to 40° C.) induces relaxation of the fasciae by reducing viscosity and making the tissue softer and more pliable. Accumulation of metabolic byproducts can increase the acidity of fasciae which thereby causes dysfunctional or less elastic fascia owing to an increase in hyaluronic acid viscosity. This increase is associated with a reduction in the lubricity of ground substance.

Myofascial decompression therapy increases the volume of tissue in the musculoskeletal system and reconfigures the structural and biochemical features of the ground substance between facia fibers in tissue. MFD can be accomplished through external application of a mild shearing force to soft tissue by cupping. The temperature of the tissue increases owing to energy deposition from the mechanical movement induced by the shearing force as well as exothermic metabolic processes induced thereby.

Additionally, cupping has been found to enhance blood flow, transport of fluids, and nutrient exchange within the tissues that are being treated. It also stimulates the body's lymphatic system to remove interstitial fluids (fluid between blood vessels and cells). Enhanced fluidity of facia can improve gliding and mobility of fiber layers in the tissue and can ameliorate pain arising from stiffness and/or injury.

One mechanism through which MFD can attenuate pain may be related to the body's endogenous pain relievers, "enkephalins" and "endorphins". Tissue injury can stimulate a release of endorphins in the brain and enkephalin in the brain stem. Endorphins inhibit the propagation of pain signal by binding to mu-opioid pain receptors and reducing the level of pain signal in the nociceptor cells and the spinal cells. Enkephalins bind to delta-opioid pain receptors and block the transmission of pain in spinal cord. Additionally, enkephalins act to attenuate pain transmission to the brain by decreasing "substance P" release, a positive regulator of pain sensation in the spinal cord. It has been suggested that MFD may, at least in part, reduce pain by stimulating endorphin release.

The "gate control theory of pain" (see "Pain mechanisms: a new theory" by Melzack R, Wall P D, Science, 1965, 150:971-9, which is hereby incorporated by reference in its entirety) provides another mechanism through which MFD may modulate pain. According to this theory, a new stimulus can block and/or reduce the processing of pain information from a primary pain source via modulating the activity of projection neurons involved in transmitting pain message to the brain by activating inhibitory interneurons in the spinal cord. A noxious stimulus including mechanical (pressure, touch or pinch), heat, and chemicals can activate pain receptors in peripheral tissues. This information is transmitted to different group of sensory neurons depending on the types of stimulus in the spinal cord and then transmitted to brain via projection neurons. In MFD, the primary source of discomfort is a myofascial pain emanating from one of the MTPs in the body. Application of a subatmospheric pressure to the skin produces a secondary stimulus that may activate mechanosensory neurons that make connection with inhibitory interneurons in the spinal cord. These inhibitory neurons inhibit the activity of the projection neurons that process the pain signal from an MTP. Overall, such an inhibitory mechanism in the spinal cord act is proposed to as a "gate" operable to selectively process pain information from peripheral tissues to brain and modulate the sensation and perception of pain.

Although details of the mechanisms by which MFD mediates tissue repair and regeneration are not well understood, it is well-established that tissue reconfigurations ensue, and that MFD can improve the recovery of soft tissue injuries and various symptoms associated with injuries, including movement impairments, pain, and muscle stiffness etc.

In prior art MFD therapy, a cup is placed over a skin area, air is pumped out of the cup with a simple hand pump to provide an unknown subatmospheric pressure, and pumping is subsequently discontinued (the pump is often disconnected after a pumpdown). Prior art MFD apparatus has had no means to measure, or even maintain the (unknown) initial pressure in a cup during treatment. As well, there has been no means to apply a specific value of pressure, change a value of subatmospheric treatment pressure while performing a treatment, or to maintain and/or control the specific value and/or change. Furthermore, prior art apparatus and methods had no means to select, control, or optimize an interval of time for the application of a subatmospheric treatment pressure. Owing to the absence of control and measurement, there has been no objective way to characterize the effects of specific pressure values on treatment efficacy, or to select and/or optimize the duration of a treatment step. Accordingly, practitioners had no means to optimize a cupping pressure and time, and it was difficult to avoid an application of excessive vacuum that can cause telangiectasias, and infection.

Apart from having no measurement or control capability, prior art cupping pressure has been subject to uncontrolled variability arising from atmospheric air leaks through the perimeter where a cup is in contact with skin. Furthermore, even if the perimeter made a vacuum tight seal, the skin itself can be a "virtual" leak owing to the uncontrolled flux of moisture (including perspiration), gases, and volatile organic compounds permeating through skin and pores into the cup. In prior art practice, a cup can frequently detach from the skin when a patient moves, and/or because of leaks. With respect to having uncontrolled pressure, prolonged application of a high level of differential pressure force to the skin (and extrusion of underlying tissue in to the cup) can be painful, apart from causing chronic bruising. Bruising is believed to arise from the entrapment of blood under the skin and/or evolving rupture of small blood vessels in the extruded tissue. Moreover, repeatedly placing, replacing (in case cup detaches from the skin area) and manually pumping down cups requires substantial physical effort and time.

As regards the therapist/practitioner, some practitioners have experienced carpal tunnel syndrome caused in whole and/or part by repeatedly pumping cups with a hand pump, and placing/pulling cups from patients.

Prior art practitioners have attempted to lessen the impact of leaks and friction between cups and the skin by applying various lubricants to the skin of a patient and/or sealing edge of a cup. However low volatility vacuum greases/lubricants are generally non-aqueous and relatively difficult to remove. Furthermore, many of these substances can cause irritation and exposure to the chemical ingredients can induce harmful side-effects. Aqueous and/or soluble lubricants, on the other hand, tend to emit vapor as they evaporate or desorb volatile components. The application of greases and oils for cupping has found poor acceptance.

Transcutaneous electrical nerve stimulation (TENS) and electrical muscle stimulators (EMS)/neuromuscular electric stimulation (NMES) are two commonly used noninvasive treatment modalities useful to reduce acute and chronic pain and increase muscle strength and dysfunctions. Both of these modalities depend on the principle that neurons and muscle cells can be excited by electric stimuli. Applying a voltage to tissue can switch these cells from a "resting state" to an active or "excitable" state. Generally every body cell has a cell-type specific resting membrane potential, e,g, the electrical potential difference between the inside and outside of the cellular membrane. For example, the resting membrane potential of neurons is typically about-70 mV whereas the resting membrane potential of muscle cells is approximately-90 mV.

Unlike various other cells in the body, neurons and muscle cells can generate an action potential (a rapid, sudden, transitory, and propagating change in the resting membrane potential) upon application of an electrical and/or chemical stimulus. Communication between neurons and/or muscles is effectuated through propagation of the action potential. An action potential can modulate the structural and functional properties of neurons and muscles, and their connected neighboring cells. For example, cell-cell communications through an action potential can induce movements or mediate cognitive activities, depending on the position and magnitude of a stimulus. A propagating wave of an action potential mediates voluntary movements of an arm or a leg. In other cases, a pain signal from a peripheral injury is sent to the brain via a propagating action potential wave originating in sensory neurons.

A TENS apparatus can apply a voltage/current waveform through electrodes in contact with different portions of skin. This waveform can stimulate neurons and nerve bundles in tissue through which current flows, and propagation of the signal along other nerve fibers activates muscle cells coupled to the stimulated neurons. Activating specific neurons underneath the affected skin area of a patient to obtain an intended treatment effect depends on careful selection of the characteristic parameters defining the electrical stimulus. Electrical stimulation parameters can include an applied voltage or current pulse waveform, electrical field intensity (V/m) and/or current (mA), pulse (waveform repetition) frequency (Hz), and duty cycle (portion of the waveform during which current is injected through the skin during each pulse). TENS can be performed using relatively low or high frequency stimuli. A low frequency TENS waveform can be unipolar or bipolar, e.g. AC or DC, have a pulse frequency of 10 Hz or less, a pulse duration of 150 us and/or longer (up to about 900 ms), and an intensity selected to provide visible muscle twitch. In some applications, a low frequency TENS treatment can be maintained for about 5 to 15 min. However, a duration of 15 to 45 minutes can be preferable for some treatments, depending on the stimulation parameters, target area of treatment, and the condition being treated. A relatively high frequency TENS waveform can also be unipolar or bipolar. High frequency TENS is generally performed using a pulse rate of at approximately 50 Hz or greater, which is often selected to be within a range of about 80 to 110 Hz. A pulse duration in high frequency TENS therapy is often in the range of approximately 50 to 100 μs, although longer pulses can be useful, depending on the application. The voltage or current intensity used in a high frequency TENS treatment is often selected empirically to provoke a sensation and response to the stimulus without discomfort and/or pain. A high frequency TENS treatment to modulate pain is often applied for about 20 to 30 minutes, although treatments in the range of 5-20 minutes can be useful for some patients.

Various studies indicate that TENS treatment can increase blood vessel cross section and blood flow, which enhances the supply of nutrients and oxygen to tissue while stimulating lymphatic flow and reducing the accumulation of waste products in tissues. Some studies have shown that TENS can promote tissue repair and wound healing and improve the integrity of fascia.

EMS/NMES inject current to depolarize and activate a specific muscle(s) in the body to cause repeated muscle contractions. Muscle stimulation using EMS/NMES is believed to mimic the effects of exercise and thereby improve the muscle strength and performance. Typical the electrical stimulus parameters used for EMS/NMES include a burst modulated AC "Russian waveform", a pulse frequency in the range of 50 to 80 Hz, a pulse duration in the range of 200-800 μs. Electrical current intensity in the range of 60 to 70 mA can induce movement similar to maximum voluntary contraction in the muscle. A single a treatment duration is typically selected to result in about 10-20 strong contractions.

TENS and/or EMS/NMES devices useful to perform TENS, EMS, or both treatments are commercially available from several manufacturers (Medtronic, iReliev, TechCare, PowerDot, TENS 7000, Nue Medics, HealthmateForever, trueMedic, and others). These TENS and EMS/NMES units typically include an electrical stimulator consisting of two or more electrodes and circuitry that can provide various electrical waveform stimuli to perform a treatment. TENS and/or EMS/NMES apparatus generally utilizes adhesive electrode pads which can adhere to and inject current through selected areas of skin. A plurality of electrode pads can be used to simultaneously apply monopolar, bipolar, quadripolar, and/or complex waveform stimuli across electrode positions, depending on the application.

Typically, a simple "monopolar" treatment electrode configuration utilizes two electrodes defining a circuit through tissue, wherein one electrode induces depolarization in adjacent tissue when a current flows. A simple "bipolar" stimulus configuration can also have two electrodes defining a circuit through which an AC current flows through tissue, such that the integral total current injected is zero. A quadripolar electrode stimulus configuration can have two pairs of electrodes that are used to apply interacting stimuli provided by two independent circuits. Commercially available TENS units commonly have capability to apply various bipolar or quadripolar waveform stimuli. Most often, muscle stimulation with EMS/NMES equipment is performed using a bipolar electrode stimulus configuration.

In general, MFD, TENS, and EMS/NMES techniques and apparatus have been found to provide only modest and/or temporary relief of pain and mobility impairment for most patients. Practitioners in the art and patients have long sought treatments that provide more effective and longer term relief of pain, and treatments that can remediate impaired movement disorders. Accordingly there has been a long felt unmet need for low cost, reliable, safe and effective apparatus and treatment technology that can effectively relieve pain and/or can reduce or remediate impairment.

SUMMARY

Tissue/muscle contraction using negative pressure apparatus (subatmospheric pressure) provides faster relaxation/elongation to tissue than imposing negative pressure alone. Since tissue/muscle surfaces are multiplanar, multiple negative pressure devices and or placements are useful to cover an entire surface of tissue/muscle. Apparatus that can maintain suction at specified levels while contracting tissue makes relaxation/elongation more effective for treating impairments and decreases the likelihood of side-effect tissue damage from treatment.

Tissue contraction using negative pressure apparatus while the tissue is in a stretched position provides relatively more elongation/stretch to the tissue as compared to imposing negative pressure alone. Since tissue/muscle surfaces are multiplanar, multiple negative pressure devices and or placements are used to cover the entire surface of the tissue/muscle. An apparatus operable to maintain subatmosphic pressure at selected values while contracting tissue can enable relatively faster and/or greater relaxation/elongation that is relative more effective for treating impairments and reduces the likelihood of side-effect tissue damage.

Human joint tissue restrictions/impairments can be reduced by applying negative pressure with a negative pressure apparatus when the joint is in a restricted position are improved with contraction of the tissue. In a method of therapy, negative pressure is substantially applied to the entire joint line which induces a greater degree of improvement relative to prior art application of negative pressure to the surrounding tissue. Since tissue/muscle surfaces are multiplanar, the disclosed method can be performed using a plurality of negative pressure applicators (devices) and/or dome placements to apply negative pressure to an area substantially covering the joint. Disclosed apparatus can control and maintain suction at predetermined levels over a time period when contracting tissue makes relaxation/elongation relatively more effective for treating impairments.

Treatment apparatus operable to apply selected/preselected values of suction to skin is disclosed. The apparatus can include real time sensors operable to monitor tissue characteristics and values of physical parameters that control various treatment modalities. Various embodiments of the apparatus can provide a therapist with real time information from the sensors and can include a processor/computer operable to evaluate and/or display characteristics of the tissue being treated. The therapist or processor/computer can use the sensor data and/or characteristic tissue information to modify and/or control therapy parameters and thereby avoid or reduce side-effect tissue damage. and show tissue changes as result of the apparatus/technique. Tissue monitoring sensors in the apparatus can be based on light or sound.

Various embodiments of disclosed treatment systems and apparatus comprise one or more applicators operable to apply treatment modalities. The applicators can have sensors operable to sense quantities controlling a treatment, and/or parameters that can characterize the state of a tissue. In some embodiments, a controller or computer can effectuate a time-history treatment component applied through an individual applicator or system device. The applicators, sensors, and computer can be in a control circuit operable to maintain and/or apply predetermined values of various parameters in a treatment . . .

BRIEF DESCRIPTION OF DRAWINGS

Various embodiments are illustrated in an exemplary manner by the accompanying drawings. The drawings and accompanying description should be understood to explain principles of the embodiments rather than be limiting. Other embodiments will become apparent from the description and the drawings.

DETAILED DESCRIPTION

Figure 1:
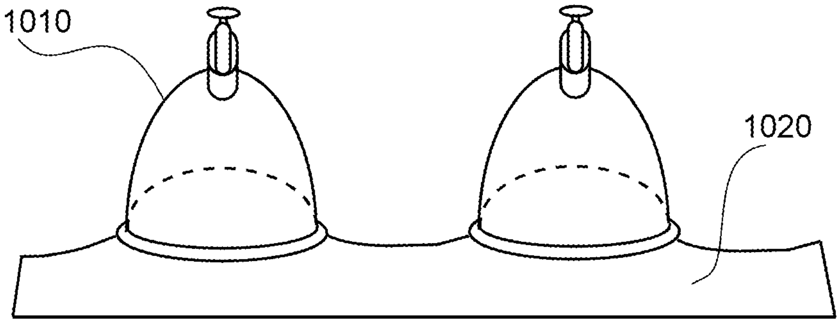
FIG.1 (Prior Art)
FIG. 1 is a diagram showing prior art cupping.
Figure 2A:
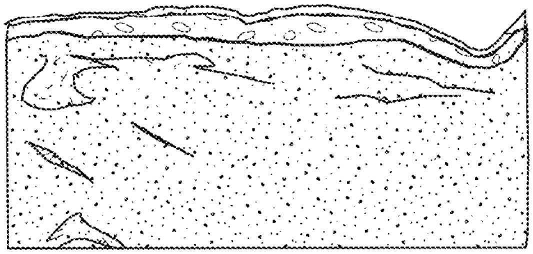
FIG. 2A (Prior Art)
FIG. 2 has exemplary drawings showing effects of cupping on skin and underlying soft tissue.
Figure 2B:
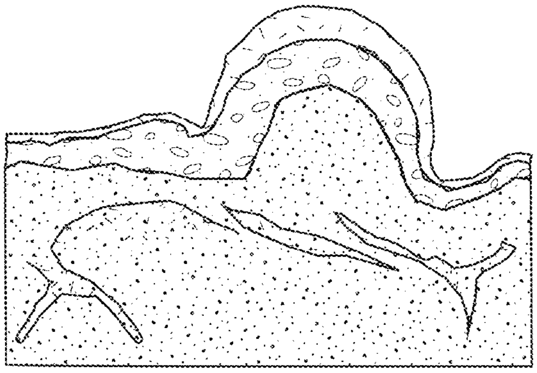
FIG. 2B (Prior Art)
Figure 2C:
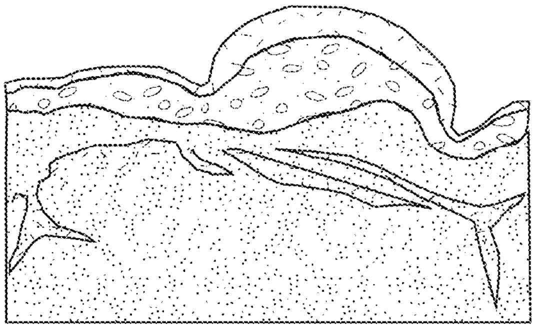
FIG. 2C (Prior Art)
Figure 3:
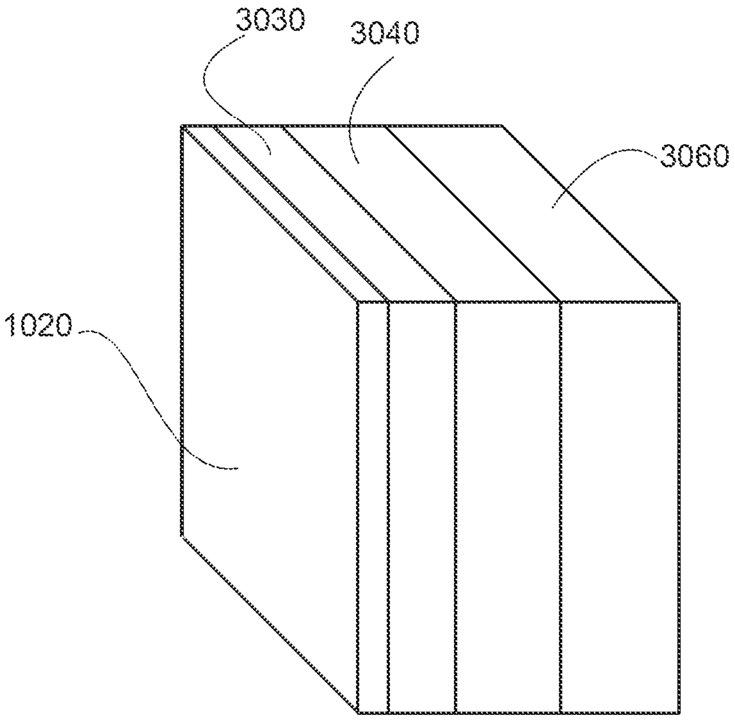
FIG. 3 is a simplified diagram showing various layers of skin and underlying tissue.
Figure 4:
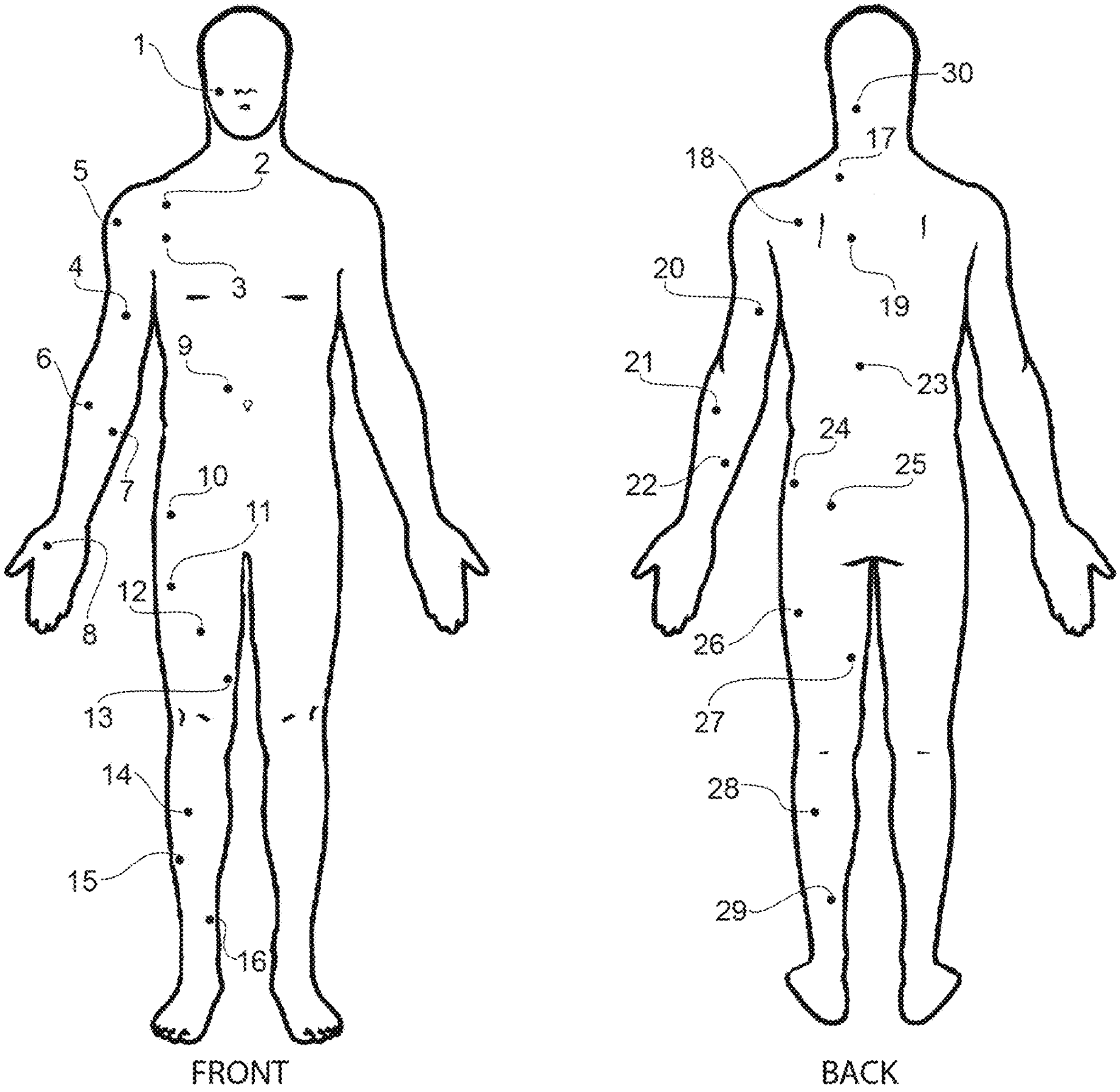
FIG. 4 is a simplified diagram showing common trigger point locations on a body.

Novel treatment methods, and apparatus for applying the treatments are disclosed. The disclosed treatments are operable to improve recovery of injured soft tissues and/or reduce pain. The treatments are particularly effective when applied to joints, muscles, neurons, tendons, ligaments, and fascia, and can alleviate various movement impairments and attenuate and/or remediate pain.

Treatment methods comprising application of a combination of driving force modalities, including without limitation localized subatmospheric pressure (e.g. differential pressure across a portion of tissue) in concert with time-varying electric voltage/currents through tissue, have been discovered to have unexpected cooperative effects. Certain treatment modalities in combination have been found to be particularly effective in stimulating soft tissue reconfiguration (FIG. 5-FIG. 8). Disclosed methods include synergistic combinations of the driving force modalities with mechanical practitioner-assisted movements (mechanical stimulus) that can be effectuated by and/or under the direction of a therapist practitioner. Various mechanical stimuli can be applied by means including "stretching", Graston™, kinesiology tape (KT), exercise regimes, body movements. and/or mechanical forces from power massage tools (electrical vibrators and similar).

Methods for diagnosing the characteristics of an injury are also provided. Various novel diagnostic methods depend on identifying a tissue contributing to pain and movement impairment (muscle, nerves, fascia and others). A number of disclosed novel methods of stimulating soft tissue reconfiguration depend on identifying location(s) of one or more trigger points associated with an injury and/or pain sensation. Trigger point location information is useful to define optimal therapies depending on synergistic effects of combinations of treatment modalities discovered to release tensions in soft tissues (MFD, TENS, EMS/NMES, certain types of exercise, instrument assisted massage therapy, kinesiology tape treatments, and others). Exemplary data relating to the assessed degree of subject patients movement impairments and pain level are disclosed. This information was used to define a patient's initial condition and demonstrate effectiveness of therapies disclosed herein.

The term soft tissue reconfiguration therapy as used herein refers to an alteration in the organization, structure, transport phenomena/properties, and/or metabolism of a soft tissue (including, by way of example, muscles, neurons, tendons, ligaments, fasciae, blood) that are effectuated using various methodologies and stimuli to facilitate recovery from an injury or impairment, and/or reduce pain. A reconfiguration therapy stimulus can be an application of external mechanical force (external fluid pressure, direct mechanical force transfer from a solid rigid, elastic, viscoelastic object, etc.), electrical current, and others by/with a therapist and/or by with prescribed self-treatment (e.g. including various exercises/movements, stretching, isotonic and isometric, contractions and others).

The term treatment modality as used herein refers to a method of applying a single kind of physical stimulus during a treatment. For example, a treatment modality can be selected from among applying a gas pressure to a tissue such as an area of skin, applying an electrical stimulus such as a voltage or current, applying electromagnetic radiation such as radiofrequency, microwave, terahertz, infrared, and/or light including ultraviolet, heating, cooling, sound such as audio and higher frequency (ultrasound/ultrasonic), physical movements including self-exercise, movements performed and/or directed by a therapist, and movement and/or mechanical forces applied through contact with an instrument such as a powered message tool, a Graston™, tool, and others.

The terminology herein is for the purpose of describing particular embodiments and is not intended to be limiting of the invention. It will be understood that, although the terms first, second, etc. may be used to describe various elements, these terms are only used to distinguish one element from another, and the elements should not be limited by these terms. For example, a first element could be termed a second element, and similarly a second element could be termed a first element, without departing from the scope of the instant description. As used herein, the singular forms "a", "an" and "the" are intended to include the plural forms as well, unless the context clearly indicates otherwise. It will be further understood that the terms "comprises," "comprising," "includes," "including," and/or "having," as used herein, are open-ended terms of art that signify the presence of stated features, integers, steps, operations, elements, and/or components, but do not preclude the presence or addition of one or more other features, integers, steps, operations, elements, components, and/or groups thereof. Reference in the specification to "one embodiment", "an embodiment", or some embodiment, etc. means that a particular feature, structure, or characteristic described in connection with the embodiment is included in at least one embodiment. The appearances of the phrase "in one embodiment" in various places in the specification are not necessarily all referring to the same embodiment, nor are separate or alternative embodiments mutually exclusive of other embodiments.

As used here, various terms denoting spatial position such as above, below, upper, lower, leftmost, rightmost and the like are to be understood in a relative sense. The various aspects of the apparatuses described herein are operable without regard to the spatial orientation of the apparatuses as a whole. For example, an apparatus can be configured in a vertical orientation or in a horizontal orientation. Hence a component or module that is described as being above another component or module in a first embodiment having a first orientation, could equivalently be described as being to the left of the other component or module in an equivalent second embodiment configured to be in a second orientation 90 degrees counterclockwise with respect to the first.

The term module refers to a distinct unit that is operable to perform an identifiable function. A module can be a self-contained physical unit or piece of equipment. A module can also be a logical component effectuated by a processor and tangible media having instructions and/or data that are operable for the processor to perform the identifiable function. The term automatic refers to a module, service, or control system that is operable to perform with no human interaction. Monitoring or sensing refers to measuring a physical quantity. Monitoring is often performed for the purpose of regulation or control.

Figure 5A:
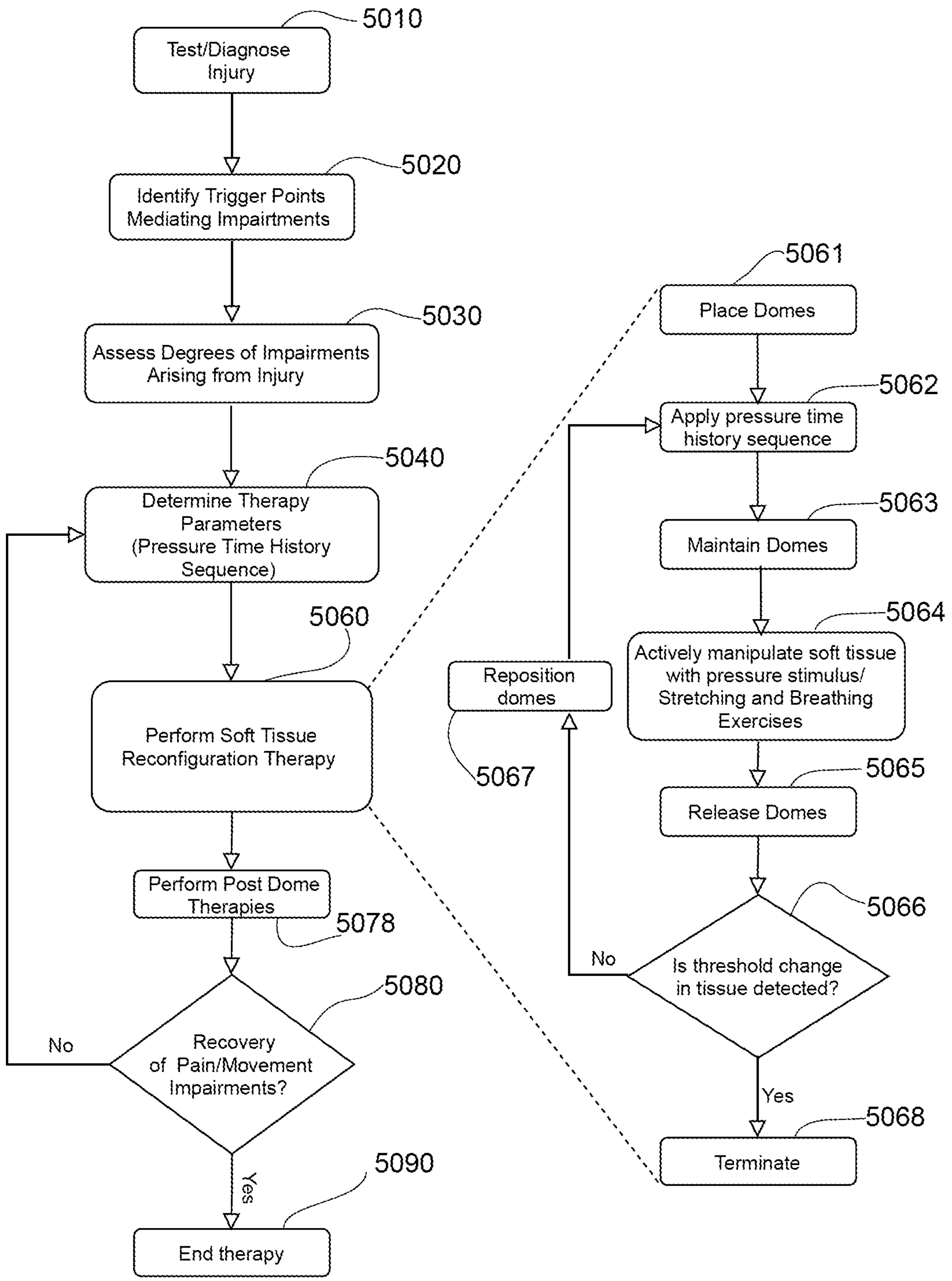
FIG. 5A is a simplified a flowchart of a treatment that can reconfigure soft tissue with an application of subatmospheric pressure.
Figure 5B:
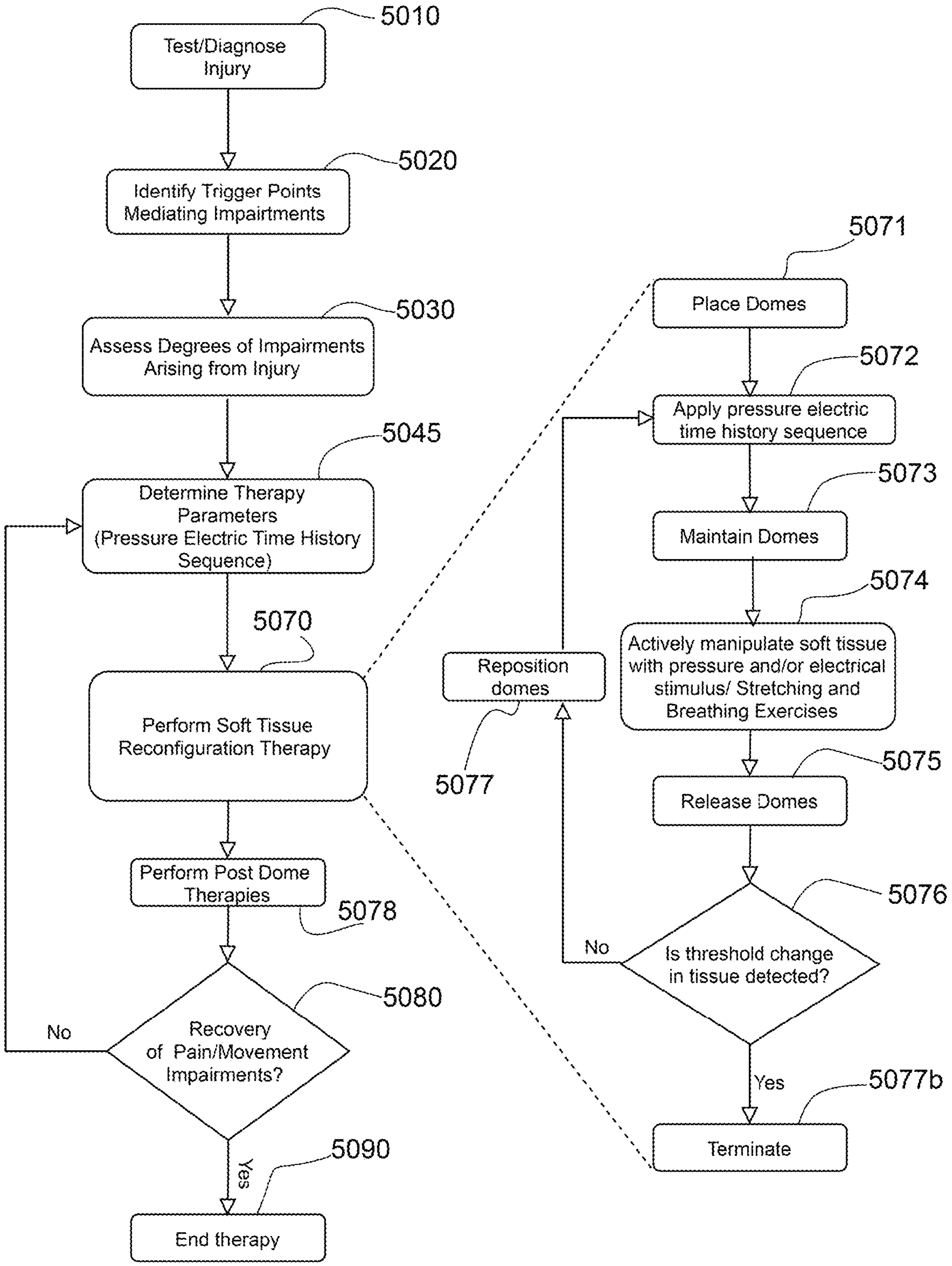
FIG. 5B is a simplified a flowchart showing portions of a method for reconfiguring soft tissue using a combination of pressure and electrical stimuli.

In various embodiments, the present disclosure provides a patient specific methodology to reconfigure an injured soft tissue using combination of a pressure, and/or electrical stimulus, and exercise to improve a patient having an identifiable movement impairment and/or pain (FIG. 5A and FIG. 5B). As shown in the simplified flow charts of FIGS. 5A and 5B, various steps of performing a patient specific soft tissue reconfiguration therapy include a diagnosis of patient's injury and/or pain at step 5010, an identification of trigger point(s) causing pain and/or movement limitations at step 5020, an assessment of the degrees of patient's impairments at step 5030, and a determination of suitable therapy parameters including definition of a pressure and time history sequence shown at step 5040 in FIG. 5A. The soft tissue reconfiguration therapy including a subatmospheric pressure treatment modality at step 5060 in FIG. 5A is performed according to steps 5061 to 5068: At step 5061 in FIG. 5A, domes operable to apply subatmospheric pressure are positioned to surround preselected skin areas extending over one or more trigger points on a patient. A predetermined subatmospheric pressure time history sequence is initiated at step 5062 and maintained through the sequenced time interval at step 5063 in FIG. 5A. Injured soft tissue is manipulated actively using a predetermined pressure stimulus in combination of a suitable exercises/movements, stretching, isotonic and isometric contractions, and breathing exercises at step 5064 in FIG. 5A. The domes are released at step 5065 ("release" means that dome pressures are gradually increased to atmospheric pressure to allow detachment) and the characteristics of the injured tissue (tenderness, tensions, and contractions) are examined at step 5066 in FIG. 5A. Depending on the change detected in the injured tissue at step 5066, the domes can be repositioned at step 5067 and the soft tissue reconfiguration therapy can be repeated or terminated at step 5068 in FIG. 5A. At step 5078 in FIGS. 5A and 5B, depending on the patient's condition, one or more post dome therapies such as an instrument assisted or manual massage therapy, kinesiology therapeutic (KT) tape treatment, a suitable exercise plan can follow the subatmospheric pressure soft tissue reconfiguration therapy. Subsequently, the performance and the pain relief of the patient can be evaluated at step 5080 to determine a degree of recovery and decide whether to terminate therapy at step 5090 or apply further therapy at step 5040 in FIG. 5A and step 5045 in 5B.

In further embodiments, a soft tissue reconfiguration therapy method includes applying a synergistic combination of pressure and electrical stimulation simultaneously or sequentially to a selected skin area of a patient covering a trigger point with a dome operable to apply selected values of voltage or current and subatmospheric pressure stimuli (FIG. 5B, FIG. 7A-B and FIG. 8A-B). Adjustable treatment parameters for the therapy include values of pressure, electrical parameters (voltage/current waveform), and a time history sequence for their application shown at step 5045 in the flow chart in FIG. 5B. Appropriate values of these parameters can based on standard prior art guideline ranges known to practitioners, or preferably, suitable parameter ranges disclosed herein. A method of performing a soft tissue configuration using subatmospheric pressure and electrical treatment modalities can include steps 5070 and 5071-5077*b* of FIG. 5B. Injured tissue and/or a trigger point can be actively manipulated using preselected levels of subatmospheric pressure and electrical stimuli (e.g. voltage/current waveforms) in combination with specific exercises/movements, stretching, isotonic and isometric contractions, and breathing exercises shown at step 5074 in FIG. 5B.

Diagnosis of an injury at step 5010 in the flow chart in FIG. 5A and FIG. 5B is one of the critical steps to define an effective therapy comprising the application of simultaneous and/or sequential treatment modalities in concert to treat a movement impairment and/or pain. Diagnosis of the patient's injury can be based on information concerning the temporal and spatial characteristics of the injury (specific movement impairments, pain, tenderness, stiffness, numbness, and others), the chronology of the injury and symptoms, any environmental stimuli, conditions and/or activities that modify sensations arising from the impairment, and/or a characteristic of the impairment (for example a particular movement impairment, and/or a posture may limit subsequent movement or modulate pain, etc.).

The temporal aspects of an injury comprise the duration, frequency, and intensity of the symptoms described or reported by the patient and the patient's doctor. For example, one of the symptoms of a patient can be a pain that may be constant and/or can occur certain frequencies with a repetitive manner or it can be associated with certain movements and/or certain activities. Duration of a pain can differ from minutes to hours, days, or weeks. Severity and duration of the pain can depend on the location of an injury.

In an embodiment, a method of identifying of the regions where the pain comes from is disclosed. This method includes examination of the characteristics of the pain particularly if it is caused by muscles, neurons, ligaments, tendons, and fascia and if the pain occurs in one or more places and whether it spreads other locations. For example, a muscular pain can be assessed by stretching the muscle and/or putting a source of resistance on the muscle and monitoring the degree of pain. If it is a pain due to the injury of nerves, the stretched affected area of the body causes more pain. Injuries related to fascia generally causes localized pain. Moving a joint to its end range of motion normally do not cause pain. If the patient has experiencing pain while performing a full range of joint motion or passive stretching, the patient may have a joint pain.

Additional information useful for diagnosis includes the chronology of the injury and pain, negative and positive regulators of the pain, other symptoms of the patient and if these symptoms are somehow linked to the injury described by the patients. Generally, physician's, physical therapist's and/or practitioner's broad knowledge on human anatomy, the kinetics of body movements, understanding of pain sensation and perception, and their previous experience on diagnosis serve as valuable assets to identify the key aspects of the injury and potential cause(s) of the injury and its symptoms accurately and propose a personalized effective treatment strategy for a patient.

The injured body region of a patient can have one or more trigger points causing pain, movement impairment and/or other discomforts. Trigger points associated with pain and/or movement impairments are identified at step 5020 (FIG. 5A and FIG. 5B) either by physical examination of the injured tissue and/or more sophisticated imaging. Palpation technique is a commonly used physical examination method to access the characteristics of the soft tissue including tenderness, stiffness, and plasticity. A therapist identifies (and validates) the trigger points by touching the injured tissue of a patient by fingers and hands and evaluating the tenderness, scar mobility, fascial adhesion, hypertonicity, and an induction of pain. Typically, the trigger points are tender and elicit varying degree of pain when exposure to a direct mechanical force such as touching. Physical examination continues with the surrounding areas (distal, medial, lateral, anterior, and posterior regions) of the injured tissue to identify additional trigger points involved in pain and/or movement impairment.

Various imaging techniques including advanced ultrasound or magnetic resonance imaging-based tissue imaging techniques such as gray scale imaging, Doppler imaging, elastrographic ultrasound imaging, tactile sensors, and/or tactile imaging techniques can also be used to identify trigger points. These imaging techniques provide information about the characteristics of the tissue including elasticity and stiffness. However, they are relatively expensive and have limited availability.

Injuries often decrease the plasticity and functional characteristics of tissues and cause pain and/or movement impairments. Stiffness, rigidity, tension, and reduced strength in tissues owing to injury, diseases or aging can decrease individual's potential ranges of motions (the total degree of motion covered by a joint moved by active muscle contraction, passive movements and/or both) and mobility. The degree of patient's pain and mobility impairments are accessed before the therapy session starts at step 5030 (FIG. 5A and FIG. 5B). The degree of pain is evaluated by a numerical scale (from 0 to 10 where 0 indicates no pain and 10 indicates maximum pain) or categorical scale (for example none, mild discomfort, moderate pain, and severe discomfort and pain) based on patient's own rank. A standard manual muscle test procedures are used to quantify a patient's ranges of motions and movement impairments (Muscles Testing and Function with Posture and Pain, Florence Peterson Kendall, Elizabeth Kendall McCreary, Patricia Geise Provance, Mary Mcintyre Rodgers, William Romani, 2005, Lippincott Williams & Wilkins, hereby incorporated by references in its entirety for all purposes). Muscle strength can be accessed by observing muscle contractions and the range of motions with and without gravity and/or applied resistance. Depending on the injury type, various tests can be adopted to quantify the limitations in a patient's muscle reflexes, tone, and sensation. Active and passive ranges of patients' motion are measured according to standard guidelines for joint motion measurement (Measurement of Joint Motion: A Guide to Goniometry, Cynthia C. Norkin and D. Joyce White, 2016, F. A. Davis Company, hereby incorporated by reference in its entirety for all purposes). Depending on patients' movement impairments, one or more of various angular movements of the body parts such as flexion and extension at the shoulder and knees, the neck, the vertebral column, abduction, adduction and circumduction of the upper limp at the shoulder, and the rotation of the head, neck, and lower limb and other can be determined to quantitate movement impairments and keep track of the progress in recovery after the treatment.

Figure 6:
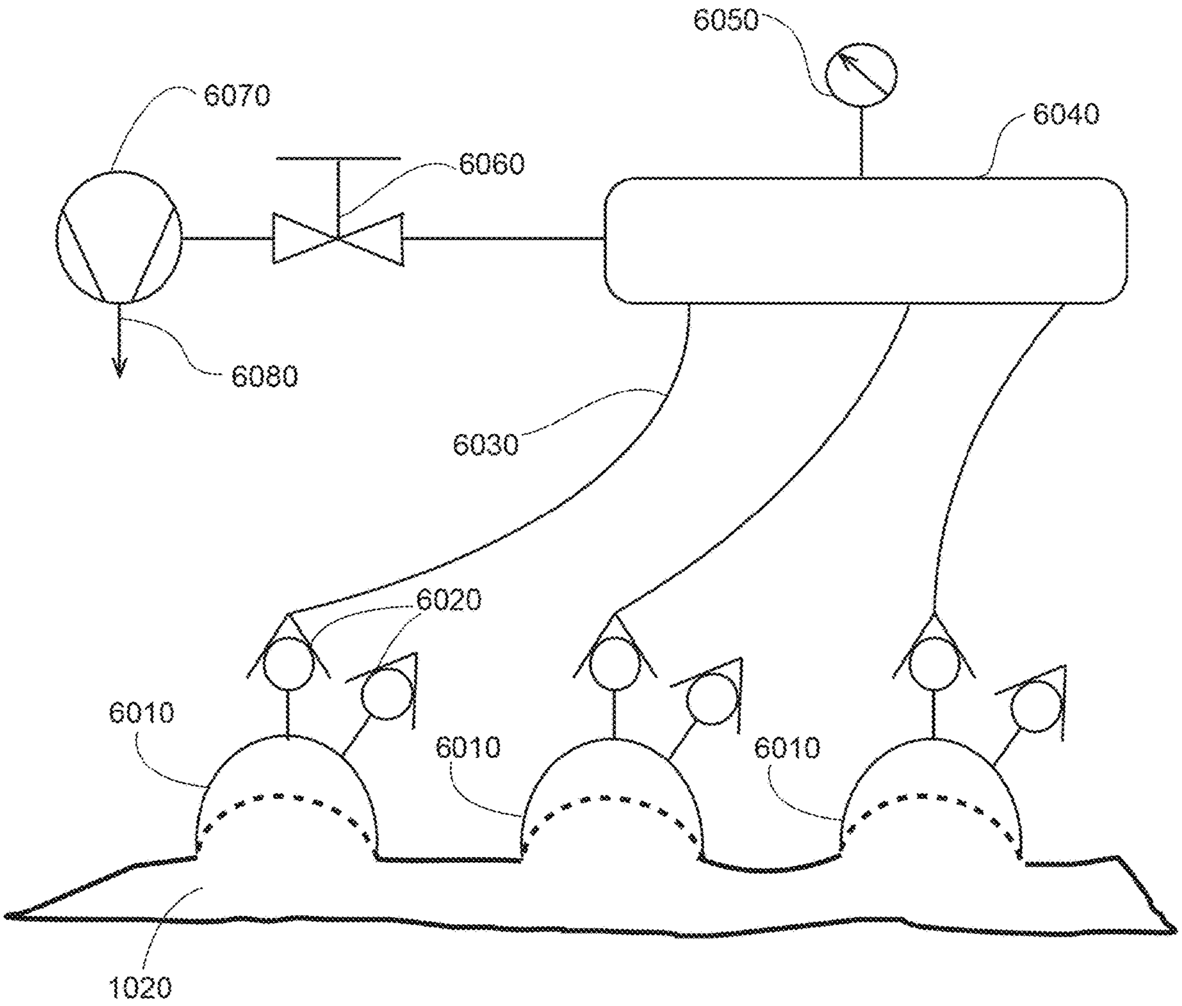
FIG. 6 shows a simplified diagram of a system and method of soft tissue reconfiguration therapy using subatmospheric pressure applied through a dome.

In various embodiments, disclosed methods include placing, maintaining, and releasing one or more domes on a selected skin area of a patient covering one or more identified trigger points (at steps 5060, 5061-5068 and steps 5070, 5071-5077*b* seen in the flow charts in FIGS. 5A and 5B respectively, and FIG. 6).

FIG. 6 has a simplified diagram of an apparatus that can be used to apply soft tissue reconfiguration therapy using subatmospheric pressure. The apparatus has at least one dome 6010. A dome has at least one check valve 6020 through which air can enter. A second check valve according to FIG. 6 can be opened to the atmosphere to admit air for release. A dome is an enclosure configured to make sealing contact with a curved area of skin on a patient. The base of a dome compromises a circular, elliptical, or saddle shape closed curve. The base can be flat and/or be adopted to the surface of a skin 1020 in different parts of the body using elastomeric materials that can fit into skin and body curvature better. Advantages of using elastomeric materials such as silicone and others on the base of a dome include relatively more uniform distribution of pressure in a skin area covered by a dome, and relatively better sealing contact with the skin. This provides less gas leakage and relatively more stable preselected subatmospheric pressure during the time interval of a treatment as compared to prior domes made of a rigid material. The dome can be in different sizes depending on the injured tissue. A dome according to FIG. 6 can have a second check valve that is operable to be opened to atmospheric pressure to release the dome from a patient. Each dome is connected to a vacuum manifold 6040 with a sealable tubing 6030 to minimize the gas leakage problems. A pressure sensor 6050 can be configured to monitor a pressure level in the manifold. The vacuum manifold is sealingly coupled to a vacuum pump 6070 via a pressure control valve 6060 which maintains a selected pressure in the manifold. The pressure of air in the dome can equilibrate with the manifold pressure to provide a selected value of subatmospheric pressure in each dome for therapy.

In various embodiments, domes are placed over the skin areas of a patient covering and surrounding the identified trigger points at step 5061 in FIG. 5A or at step 5071 in FIG. 5B. The strategy to position of the domes on a skin area covering the identified trigger points depend on the position, size and shape of an injured tissue, the orientation of the fibers in an injured tissue, and nearby landmark bones around the injured tissue. Tissue size in human body various significantly depending on the body location. Generally, deep tissues require bigger dome size compared to ones for the shallow tissue to capture the tissue and the surrounding fascia more effectively. The dome sizes from 0.5 to 3.5 inches in inner diameter are commercially available from various manufacturers.

When exposing skin to a subatmospheric pressure (vacuum) and thereby apply differential pressure to tissue, the levels of pressure and duration of treatments are critical parameters for tissue reconfiguration therapy. The level of subatmospheric pressure and length of time for a treatment step can be preselected to optimize the effectiveness of treatment and minimize undesirable side effects including tissue damage (i.e. bruising, skin irritation/rupture, pain). In our experience, there are highly nonlinear interactions between the control variables, which include number and position(s) of dome(s), subatmospheric pressure level (value), treatment step duration, dome size. The greater the differential pressure applied (low the subatmospheric pressure) and the longer the treatment step, the greater the probability of various types of tissue damage. The predetermined values of these treatment variables are selected using guidelines determined from prior experience in treating various different tissue structures and types of injury. Response of the tissue, skin reactions, and/or evolution of bruising where the domes are placed should be monitored during treatment.

In various embodiments, these therapies can include additional simultaneous and/or sequential application of predetermined movement elements and/or exercises. Here, unlike prior art treatment where domes tended to leak and fall off, the constant and consistent dome pressure(s) being actively maintained throughout a treatment keeps the dome (s) in place and not detach from the skin, even where movement therapy is being simultaneous performed. For example, in some therapies, a therapy can comprise 5 or 6 domes maintaining a subatmospheric pressure of 50 kPa over trigger points on a patient's thigh muscle, vastus lateralis while a patient lies stationary on a treatment table and a practitioner moves the patient's right leg to a preselected direction according to the patient's movement restriction. In some embodiments, a simultaneous breathing exercise can additionally be imposed or induced by a practitioner. Without active pressure control, body movements and/or gas leaks made it difficult or impractical to maintain a constant pressure and retain the domes in place for a predefined treatment interval.

In some further embodiments, a therapy can include steps comprising a subatmospheric pressure time history see FIG. 5A, step 5040 and/or simultaneous or sequential active and/or passive movements at step 5064.

In various embodiments, a commercially available vacuum pump operable to generate a subatmospheric pressure in a range of 0.0013-1 atm (1-760 Torr) such as Kendal HB-SFD02 vacuum pump is used to perform a soft tissue reconfiguration therapy using domes.

Gas leaks at various connection points of the therapy ensemble and the rate at which volatile compounds released from the skin can affect the level of the predetermined subatmospheric pressure in a dome at which the therapy is being performed. Leakage can occur through the contact areas between the skin and the dome. Elastic property of the skin can seal the dome to some extent and allow the dome remain at the desired position of the body for a preselected time interval during the therapy. The amount of leakage can be large if the injured region of the body has a different curvature compared to the base of the dome. In such cases, the maintenance of the predetermined subatmospheric pressure for a preselected time interval of the therapy become quite difficult. In some cases, the dome can even become detached from the skin entirely. Potential leakage problems can be remediated by making all connections areas in the vacuum ensemble are fully sealed, and/or using a different size and shape of dome that fits to the curvature of the affected body area better. Alternatively, a vacuum pump can continuously run to evacuate gas from the dome during the therapy to compensate any leakage problem.

Another aspect of soft tissue reconfiguration method includes placing a number of domes over predetermined areas of skin covering selected trigger points of a patient, and simultaneously evacuating the domes, thereby adherently sealing the domes above affected body areas of a patient. This method is advantageous since it eliminates the need of using lubricants and/or lotion while positioning the domes as well as any side effects associated with some of these lubricants.

In still further embodiment, a vacuum pump without a manifold can be sealingly connected to a dome directly is disclosed to position one or more domes over a skin area including identified trigger point sequentially.

In another embodiment, the time interval of application of a subatmospheric pressure in domes is determined between 15 and 150 seconds which provides an intended structural and physiological changes in the affected area to increase blood supply, and facilitate nutrient and oxygen exchange and modulate the elasticity characteristics of the soft tissue without causing a tissue damage. In further embodiment, the partial or full restoration of patient's movement impairments, strength, and level of pain after the therapy are evaluated after the therapy to monitor the effectiveness of the therapy.

In another embodiment, a predetermined value(s) of subatmospheric pressure in one or more domes positioned on the skin over trigger points and/or a preselected time interval of treatment is automated using microcontroller. The method includes a microcontroller coupled to one or more valves that can allow a gas flow entering or being evacuated from each dome automatically. There are some embodiments where the microcontroller can automatically maintain a preselected pressure in each dome. A rate of flow and time interval for pressurization can be specified before the therapy begins. In some embodiments, a timer is used to toggle between an on and off state of the control valves connected each dome. A valve can be opened or closed after a predetermined time interval.

Generally predetermined movement elements and/or stretching exercises are incorporated to soft tissue reconfiguration therapy if the patient has known movement restrictions because of the injury and/or pain. There are embodiments where the tissue reconfiguration therapy is performed in combination with one or more therapist assisted movement elements are operable to effectuate improvement where an injury limits the patient's ability to perform certain movements. In some embodiments, the tissue reconfiguration therapy using domes can be done while the patient is stationary, or stationary but combined with relevant movement elements associated with pain and/or limited by an injury and/or breathing exercises at step 5064 in FIG. 5A and at step 5074 in FIG. 5B.

In another embodiment, a subatmospheric pressure stimulus can be applied to the more sensitive tissues such as joint surfaces, neck, and face tissues. In such cases, the therapy is performed using a lower level of subatmospheric pressure differential with a shorter time interval of a treatment compared to those used for other types of soft tissues to avoid any tissue damage.

In efforts to treat joint tissue impairments more effectively, it was discovered that it is most effective to place one or more domes over an entire joint line and joint surface area while the joint being treated is in a restricted position and then applying and maintaining a predetermined subatmospheric pressure in the domes during a selected time period. Depending on the degree of a joint movement restriction and pain tolerance of a patient, a joint is held in the restricted position for about 1 to 90 seconds while subatmospheric pressure stimulus is applied over the joint of a patient in the manner described above. It was generally found that a time period of 3 seconds was effective in most cases, and a range of about 1-10 seconds was applied during a number of standard treatments.

It has been found that the tissue reconfiguration therapy, when performed with a practitioner assisted suitable movement elements improves the elongation of injured tissue significantly as compared to conventional prior art cupping methods. Practitioner assisted movement elements can induce a specific muscle in an injured tissue to contract, relax, or elongate during a predetermined time period (usually in the range of 3 to 60 seconds) and number of cycles depending on an injury type and pain tolerance of a patient. In a preferred embodiment of a treatment, 3 cycles are applied, however a number of cycles in the range of 2-10 can be useful, depending on a patient's condition. It was discovered that positioning of one or more domes on an injured tissue or an impaired joint while the muscle in a stretched position or a joint is in a restricted motion and then applying and maintaining a differential pressure stimulus on the injured tissue or the impaired joint with a repeated number of contraction and elongation of the muscle had synergistic effect compared to performing each treatment method alone. It was further discovered that even as little as 3 second of a muscle contraction due to a practitioner assisted movement elements of a patient during a reconfiguration therapy using domes releases trigger points in an injured muscle and/or facia faster and more effectively than performing the conventional cupping methods without any active muscle manipulation. The practitioner assisted movement elements during a reconfiguration therapy with subatmospheric pressure stimulus also improves the recovery of joint movements and/or range of motions of patients notably as compared to the application of each individual treatment modality separately.

In still further embodiment, a less painful method of releasing an attached dome from the skin at the end of the therapy session is disclosed at step 5065 in FIG. 5A and at step 5075 in FIG. 5B. To do this, the subatmospheric pressure in the doom is gradually increased to ambient pressure by admitting a gas flow into the doom through a gas passage in the respective dome. A gas passage can be connected to a check valve 6020 in FIG. 6 in the respective dome.

A tissue reconfiguration therapy with domes can precede various post dome therapies at step 5078 (FIG. 5A and FIG. 5B) including an instrument assisted massage therapy using Graston™, sound assisted soft tissue mobilization (SASTM), functional and kinetic treatment with rehabilitation (FAKTR), vibrational massage tools and others or alternatively KT tape-mediated mild decompression therapy. The instrument assisted massage therapy mobilizes soft tissue and modifies the structural organization of the soft tissues owing to a direct mechanical pressure applied through these instruments. Unlike the tissue reconfiguration therapy using a subatmospheric pressure stimulus, the instrument assisted massage therapy compresses the soft tissue and decreases the volume of soft tissue. This tissue decompression affects the blood circulation and lymphatic system and can promote recovery of injuries further. According to our experience, an instrument assisted massage therapy is less painful to the patients if it is applied after the tissue reconfiguration therapy using domes.

In some embodiments, a mechanical pressure stimulus using an instrument assisted massage tool such as Graston™ or vibrational massage tools proceeds the tissue reconfiguration therapy with a subatmospheric pressure stimulus to facilitate the recovery of an injured soft tissue surrounding the identified trigger points. We discovered that the order of types of therapies being applied to patients should be chosen carefully. For example, a mechanical pressure stimulus applied to the injured tissue using instrument assisted massage tools after a tissue reconfiguration therapy is less painful and more acceptable for patients than the application of these massage tools first. Furthermore, if a vibrational massage tool is used to treat an injured tissue of a patient after the sub atmospheric pressure stimulus, the injured tissue becomes noticeably less tender.

In some embodiments, a KT tape treatment can follow a tissue reconfiguration therapy using domes to mitigate the recovery of injured tissue further. KT tape has similar elasticity characteristic as skin and provides additional support for the soft tissues. KT tape increases the volume of soft tissues and stimulates the lymphoid system when applied on the muscles, ligaments, and tendons. It also helps to heal the redness and/or bruises, tenderness resulting from the differential pressure application using domes. Our experience shows that KT tape help to attenuate the tenderness and bruising of the injured tissue the following day strongly. KT tape is designed to stay on the tissue in hours or days. Therefore, it can also be beneficial to use KT tape after application of subatmospheric pressure using domes if the injury requires a longer and milder stimulus for recovery After post dome therapies such as an instrument assisted-massage therapy and/or a KT tape treatment at step 5078, the recovery (pain reduction and/or remediation of movement) of a patient at step 5080 in FIG. 5A and FIG. 5B can be assessed using standard procedures described above. Generally, if the patient's recovery is above predetermined thresholds, the therapy session ends at step 5090, shown in FIG. 5A and FIG. 5B (for pain a threshold of 50% recovery is typically used, and a threshold for movement impairment recovery is typically about 20%, although larger values such as 30% or smaller threshold values can be preferable, depending on a patient's medical history and risk factors). If a patient recovery score is below the predetermined thresholds, the parameters used in tissue reconfiguration therapy using domes and post-dome treatment options are modified at step 5040 (FIG. 5A) and at step 5045 (FIG. 5B) and the treatment continues with the modified parameters.

Figure 9:
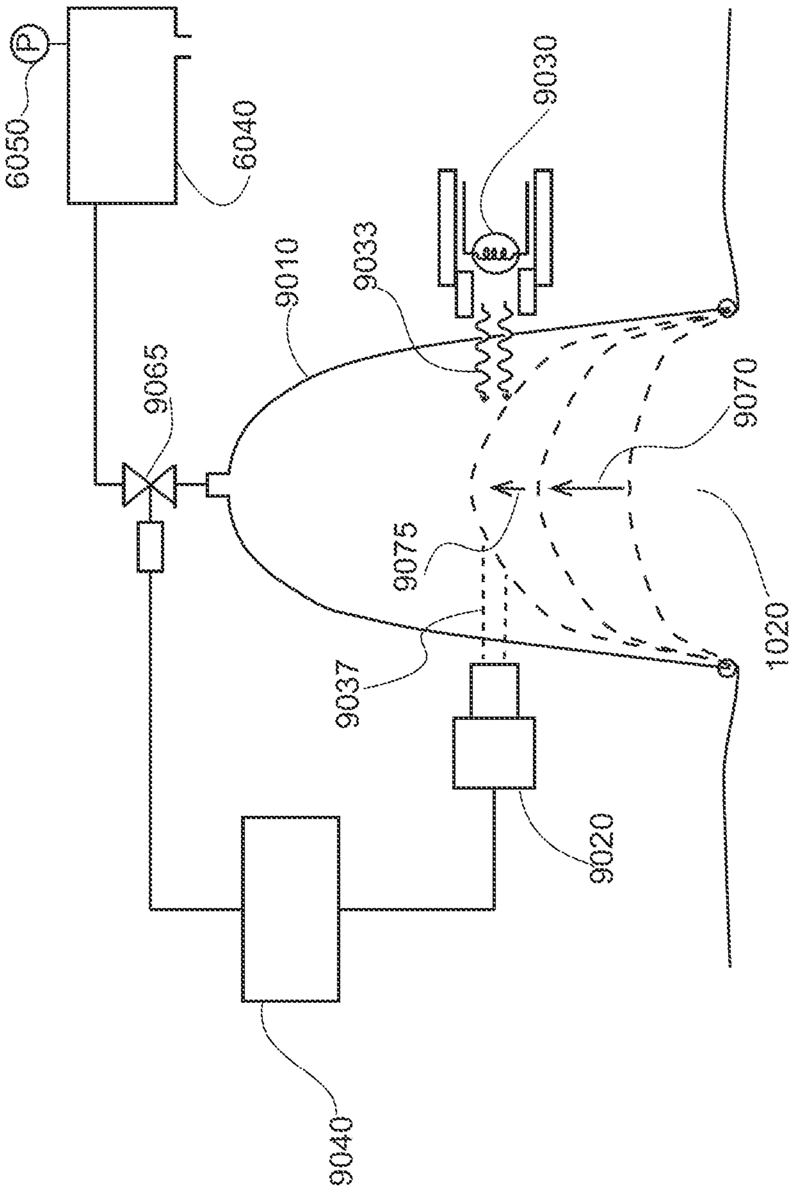
FIG. 9 is a simplified diagram of a system including a dome, light source, and a camera or photodetector.

Depending on the application, the amount of tissue distension when applying subatmospheric pressure to an area of skin can be critical parameters. Too much distension and an excessive pressure differential between the skin surface and interior of tissue can cause bruising, pain, discomfort or even trauma and permanent injury. In some embodiments distension and be controlled and/or injury avoided using a dome having sensing means (FIG. 9). For example, a dome 9010 can have a photocell type sensor to detect the height/distance 9070 or 9075 to which skin tissue is extruded into the dome. In some embodiments a photodetector 9020 can detect tissue presence through the interruption of an amount of light crossing a path through the dome from a light source 9030. The light rays from the light source 9033 is attenuated to the light rays 9037 owing to the level of distension of the tissue (FIG. 9). There are further embodiments where the photodetector 9020 can be a solid state CMOS and/or CCD camera chip operable to detect a presence and/or color (e.g. a visible wavelength, partial or full spectrum in a visible or infrared spectral region, and others) of tissue that is indicative of the state and/or existing or putative trauma from the extrusion and/or pressure stimulus. The sensing can be coupled to a control loop operable to control and/or limit an amount of extrusion or physiological indicia of tissue stimulation and/or injury. The control loop can be effectuated using a digital microprocessor 9040 and/or controller having suitable software/firmware and interfaces to the sensors and dome pressure/pumping means. The dome pressure pressure/pumping means can include an adjustable valve 9065, a manifold 6040 and a gauger 6050. In various embodiments the controlling can be performed automatically.

Unexpectedly, it has been found that treatment comprising a pressure differential stimulus induced using the tissue reconfiguration therapy via domes together with an electrical stimulus using TENS and/or MSE to manipulate the soft tissues in an affected body area of a patient can induce a therapeutic outcome significantly better when either or both treatments are separately applied at different times. Depending on the diagnosis and clinical variables, synergistic improvement has variously been found when TENS/MSE and the tissue reconfiguration therapy via dome are administered simultaneously, as well as when a combination of these treatments is applied one immediately after the other.

In various embodiments, commercially available TENS and/or MSE equipment can be adapted to apply TENS/MSE and the tissue reconfiguration therapy via a dome cooperatively to effectuate a relatively reduction in pain sensation and/or movement impairments (FIG. 5B).

Figure 7A:
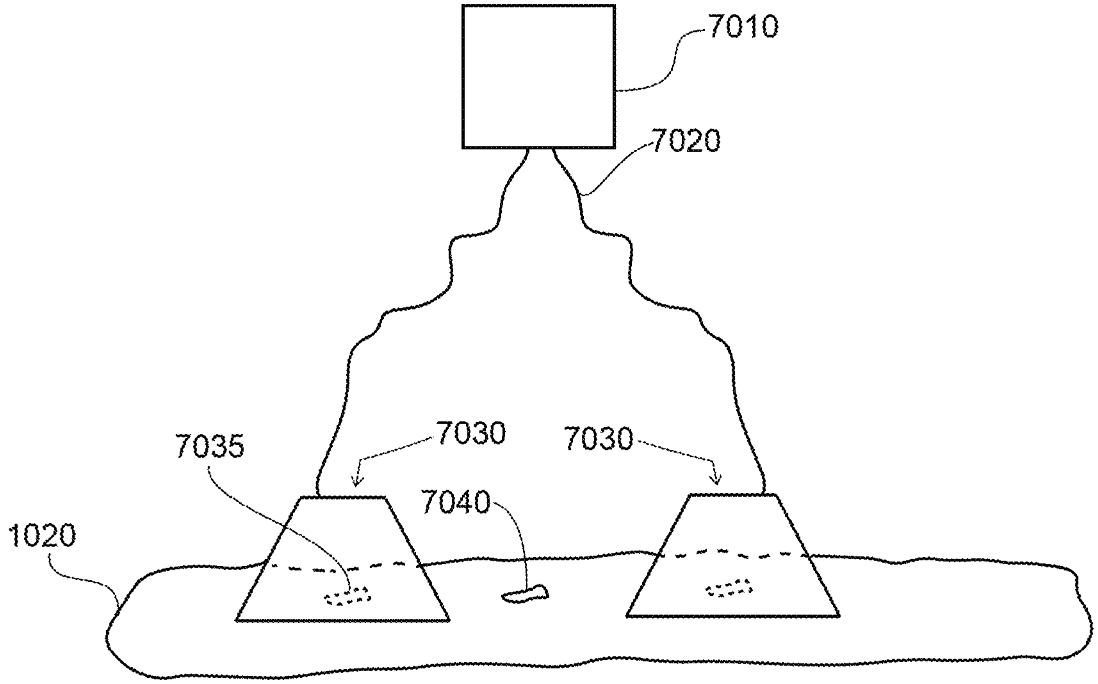
FIG. 7A shows a simplified diagram of apparatus that can apply electrical and/or subatmospheric pressure using a dome.
Figure 7B:
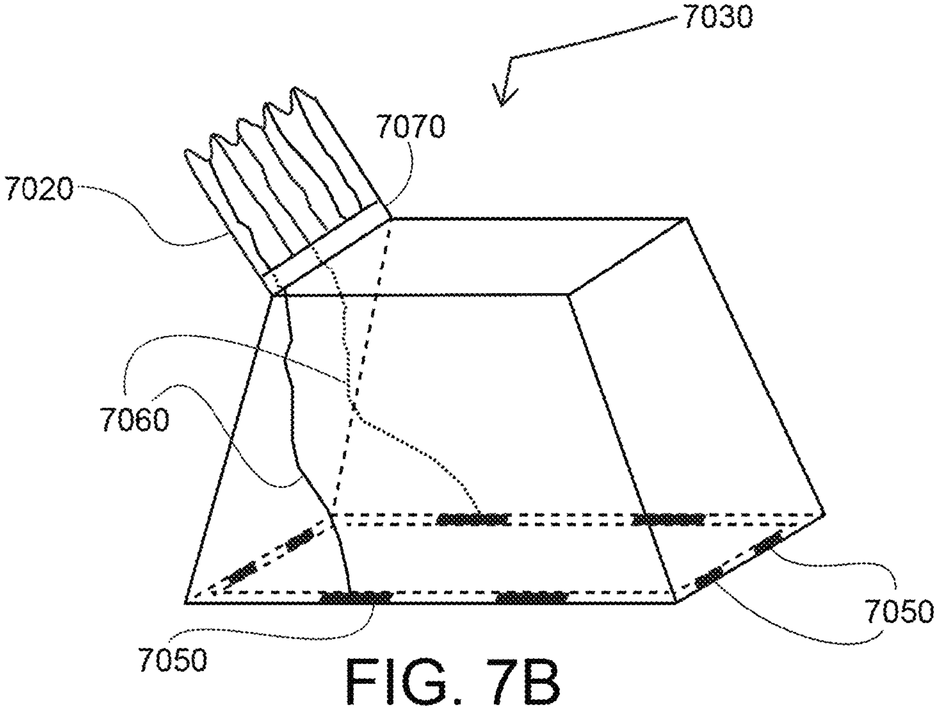
FIG. 7B shows a simplified diagram of showing a configuration of electrodes on a bottom skin contact surface of a dome.

In various embodiments, a dome 7030 can have a sealable bottom edge including a plurality of conductive electrodes 7050 operable to be electrically coupled to selected areas of proximate skin 1020 (FIG. 7A and FIG. 7B). In some embodiments the electrodes can make ohmic contact with the skin areas. In other embodiments at least some of the electrodes can have an insulating coating and can be capacitively coupled to proximate skin areas. The electrodes can be connected to a connector 7070 by conductors 7060. Such conductors can be wires, conductive tape, conductive paint, or the like. The conductors can be on a surface of a dome and/or can be embedded in dome material. These embodiments can include an electrical stimulus control and delivery unit 7010 having a cable such as a ribbon cable 7020 attached to a mating connector 7070. The electrical stimulus and control unit can selectively energize the electrodes with electrical stimulus waveforms having predetermined intensity, frequency, and waveforms selectively stimulate nerves and/or muscles. The waveforms applied to different electrodes can be in a selected phase relationship relative to one another operable to apply a preselected electrical stimulus to tissue in the neighborhood of a trigger point. In some embodiments, the trigger point can be in soft tissue circumscribed by the conductive dome 7035.

In various further embodiments, one or more stimulus waveforms can selectively energize electrodes on different domes in a selected phase relationship to apply a preselected electrical stimulus to a tissue comprising a trigger point outside of the area covered by the domes 7040.

Using suitable domes 7030, a preselected electric stimulus duration in the range of 10 and 20 minutes and a preselected subatmospheric pressure stimulus duration in the range of 15 and 30 seconds can be applied over a preselected skin area simultaneously or sequentially in a suitably selected order and duration during treatment. For example, a therapy session can begin with 1) electric and pressure differential stimuli simultaneously applied for 30 sec., followed by 2) a transition interval without a stimulus for 10 sec. before 3) electric stimulation without any pressure differential for 3 min, and finally 4) a pressure differential stimulus alone for 30 sec. (without any electrical stimulus), Depending on the patient, the above and/or various other sequences comprising stimuli applied to a trigger point in single or in combination for a selected length of time and stimulus-free transition intervals, can be repeated. One of ordinary skill in the art will recognize that electrical and/or pressure differential stimuli parameters including waveforms, amplitudes, phase relationships, pressure differential, transition time(s) and number of repetitions in a treatment will depend on a diagnosis and specific medical condition of a patient.

Figure 8A:
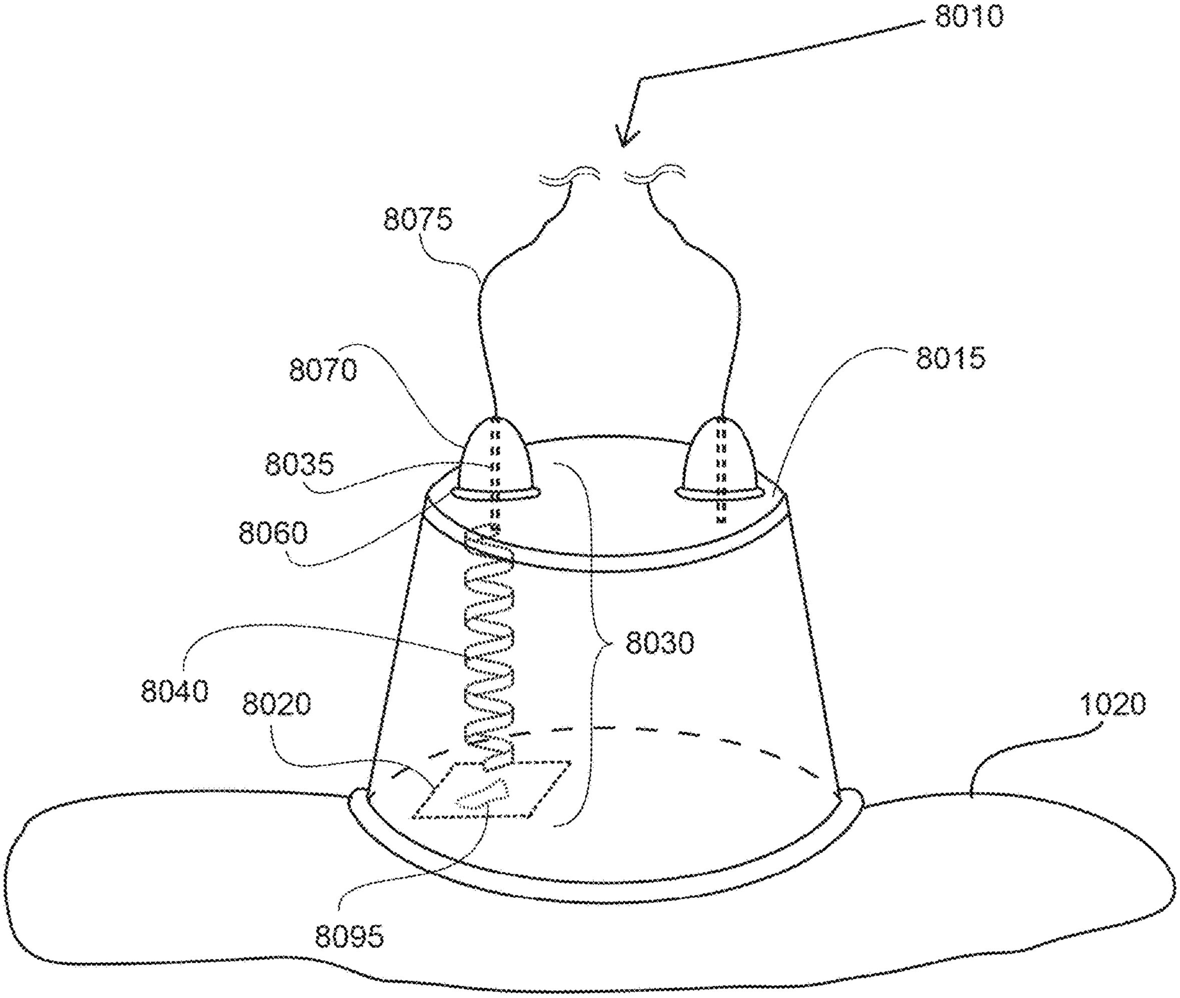
FIG. 8A is a simplified diagram of a dome including a feedthrough electrode pressing mechanism.
Figure 8B:
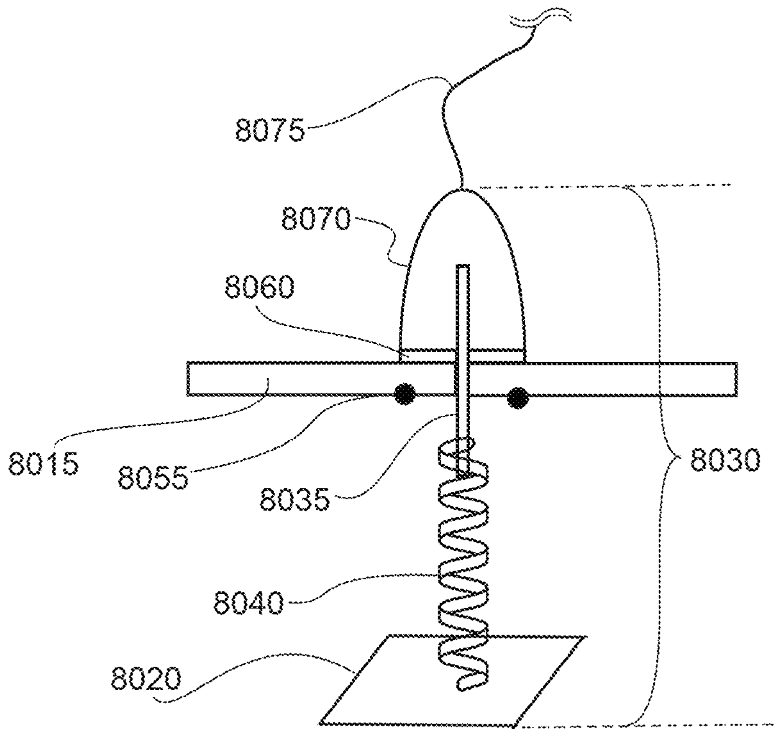
FIG. 8B is a simplified diagram of a feedthrough electrode pressing mechanism.

In another embodiment, a dome 8010 has two or more feedthrough electrode pressing mechanisms 8030 (FIG. 8A and FIG. 8B). Each feedthrough electrode pressing mechanism comprises an electrical feedthrough sealing attached to a surface 8015 of the dome 8010. The surface can be a relatively flat top surface that subtends a skin area of the subject. An adaptive conducting pressing mechanism 8030 can include a spring 8040 and/or elastomeric conductor operable to move an attached adhesive bearing electrode 8020 into stable electrical contact with a suitable skin area 8095. The conductive spring allows the electrodes to move as tissue distends responsive to the application of subatmospheric pressure, and also reduces or eliminates electrode wire entanglement within the dome. The electrodes can be in different sizes depending on the size of the dome used for modulation of a selected soft tissue.

In further embodiments, an adoptive electrode pressing system includes an electrically conductive screw stock 8035 sealingly attached to the surface of the dome using a skirt 8060 on the outer surface of the doom and an O-ring 8055 on the inner surface of the dome. The conductive screw stock is electrically connected to a connector 8070 which is attached to a wire 8075 on the outer surface of the dome to carry the preselected electrical stimulus. The wire is connected to an electric stimulus controller and power source 7010 operable to effectuate local neuronal and muscle stimulations in a selected soft tissue as mentioned above.

In some aspects, a system having an octopus-like configuration is disclosed. The system can have a control center, e.g. "head of the octopus", having one or more computer/processors and/or interfaces operable to apply therapeutic treatment sequences comprising steps of applying one or more treatment modalities to selected areas of patient tissue. Various embodiments of a therapeutic treatment sequence can alleviate pain, induce tissue reconfiguration, and/or reduce a movement impairment. A treatment modality can include the application of one or more stimuli such as a static and/or slowly changing pressure, an electrical voltage or current waveform, a temperature and/or heat flux, sound/ultrasound stimulation, and radiofrequency and/or light energy (such as ultrasound stimulation, diathermy etc.). A specific embodiment of a therapeutic treatment sequence comprises steps of applying selected treatment modalities in an order. The modalities and respective order of application can be selected to optimize a reduction of pain and/or impairment. An optimal sequence of selected treatment modalities depends on characteristic parameters of the tissue (s) being treated, as well as the medical history of an patient. In some embodiments, a treatment can comprise application of various different stimuli (e.g. different treatment modalities) to the same general portion of tissue at once and/or during one or more distinct steps in a therapeutic treatment sequence. For example, in an embodiment a subatmospheric pressure, a TENS waveform, and infrared radiation can be applied to a portion of a patient's skin during a selected time interval. In some embodiments, different stimuli can be applied during distinct and/or partially overlapping time intervals. Furthermore, depending on the characteristics of a patient and the patient impairment, a plurality of treatment modalities can be applied to two or more distinct regions of tissue simultaneously, or sequentially.

In various embodiments, a control center has a human interface operable to receive information from a therapist. The information can include characteristic patient information, treatment modalities, a treatment sequence, a treatment history, and others. A control center can receive information from applicators, various sensors, and/or a patient information database, depending on the application. In some embodiments, a control center can determine therapeutic treatment sequence based on information received from a human interface, sensors, and/or patient data from a database, depending on the application.

A treatment system apparatus can have many branches (akin to the arms and tentacles of an octopus). Each branch may support one or more treatment applicators and/or sensors. Some embodiments comprise a treatment applicator dome having at least one sensor that can monitor a stimulus intensity such as a pressure, a temperature, a wavelength or intensity of radiation, and/or others. In further embodiments, a treatment applicator can include a sensor that can monitor an effect of a treatment modality on tissue in real time. For example, there is an embodiment having an optical sensor that can sense the amount distension of a tissue responsive to subatmospheric pressure. In a further embodiment, a sensor can monitor a tissue temperature responsive to a flux of radiation. An embodiment of the apparatus can select and/or change the value of a treatment parameter in real time. In some embodiments a parameter can be controlled to have time dependent preselected values for a treatment. There are also embodiments having a control circuit operable to change the value of a treatment parameter responsive values obtained from one or more treatment sensors (e.g. sensing a tissue distension, temperature, color, texture, impedance) and/or stimulus sensors (e.g. sensing a subatmospheric pressure, radiation intensity, a voltage and/or current, applicator temperature).

In some embodiments, a treatment applicator dome can have ultrasound and/or infrared (IR) sensors that can sense a distension and characteristics of a tissue in response to subatmospheric pressure and/or other treatment stimuli. The ultrasound and IR sensors can be attached to the base of the applicator dome to monitor the alteration of tissue characteristics and volume during a therapy session. In further embodiments, a treatment applicator can have a chip to process data from a sensor partially or fully. In other embodiments, the input from a sensor of the treatment applicator can be transmitted wired or wirelessly to one or more computers for further processing depending on availability of memory and the amount of data.

In some embodiments, a treatment apparatus can have independently adjustable branches (similar to an octopus) to allow the treatment of different body parts of a patient simultaneously. The branches of the treatment apparatus can be configured to effectuate one or more treatments selected among various treatment modalities depending on the nature and characteristic of the tissue and the body parts being treated.

Prior art cups are designed to use by clinicians and/or practitioners generally as patients in a stationary position and also lack the ability to control suctions in a scalable manner, which is particularly critical when treating different tissue types and/or performing the therapy on a moving patient. For examples, the treatment of face or joints with pressure stimulus using domes requires finer control of the suction forces compared to the treatment of the hip. Furthermore, the maintenance of a traditional cups over an injured tissue of a nonstationary patient can be difficult without having proper means to control pressure within the cup.

Figure 10:
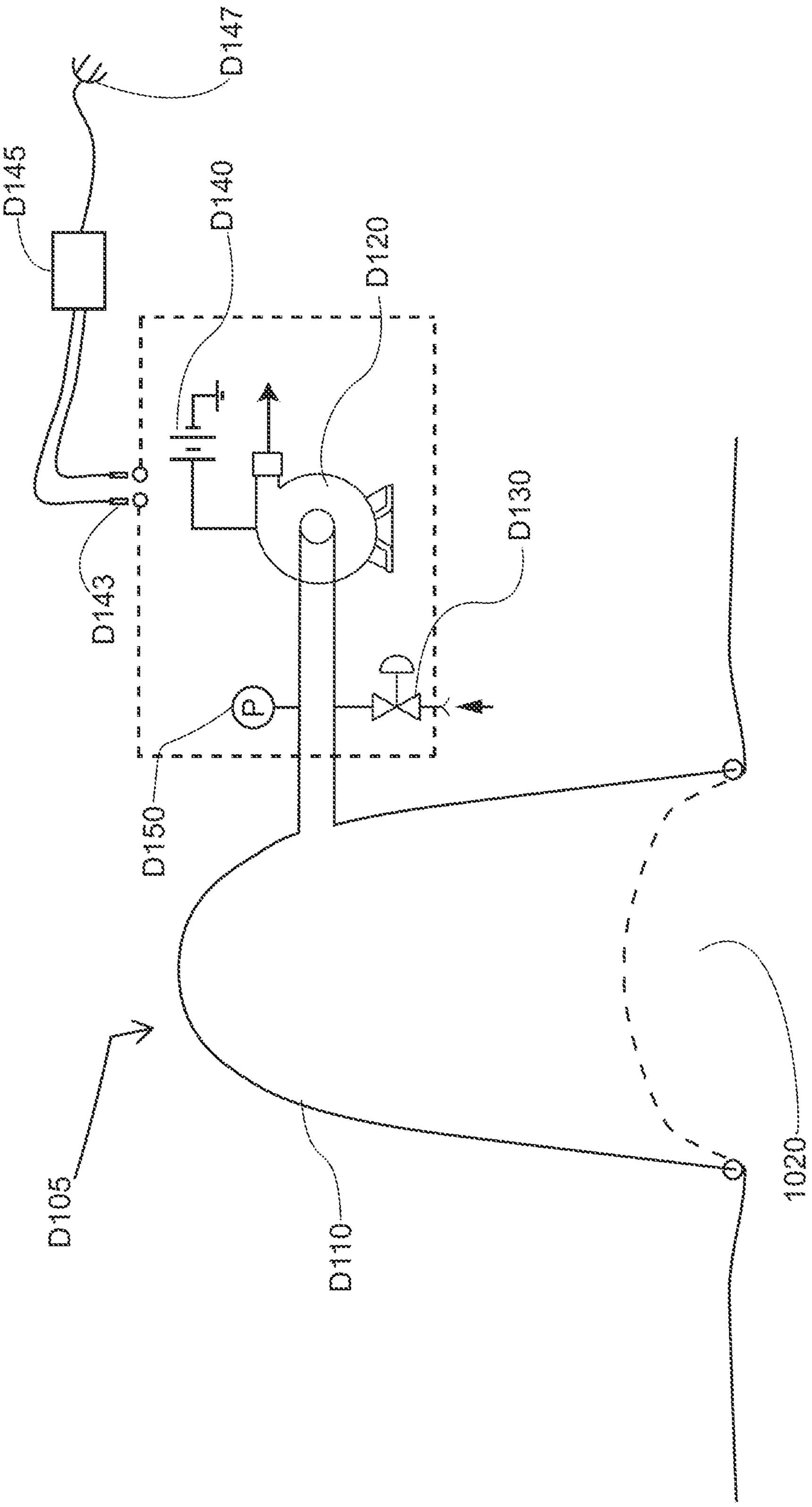
FIG. 10 is a simplified diagram of a portable dome module apparatus.

In various embodiments, a portable dome module apparatus D105 in FIG. 10 can be useful to perform tissue reconfiguration therapy by patients at home according to the instructions of the practitioners. The portable dome module apparatus can include a mini vacuum pump D120 sealingly attached to a dome D110, a sealingly attached adjustable valve D130 to regulate the pressure in the dome, and a power source D140 (FIG. 10). The pressure in the dome can be adjusted by modulating either the speed of the vacuum pump D120 or the rate of leakage of the adjustable valve D130 or both. The power source of the portable module apparatus can be a battery D140 with a charger D145 having a cable with USB D143 and a plugin D147 to plug into wall outlet directly (FIG. 10), or a wireless battery. In some embodiments, the portable dome module apparatus can have a pressure sensor D150 to monitor the pressure (FIG. 10). In further embodiments, a controller in the portable dome module apparatus can include suitable software/firmware and interfaces to the pressure sensor and dome pressure/pumping means. The controller can communicate with an iPhone, iPad and/or a portable computer wirelessly to regulate the pressure within the dome and treatment time remotely.

A self-treatment apparatus such as a portable dome module apparatus can provide a greater flexibility to patients to treat an injured tissue at home according to their own schedule once safe and effective use of the apparatus is implemented. Furthermore, the portable dome apparatus module with means of pressure regulation allows to treat patients while they perform specific impaired movement elements and/or they perform daily activities such as walking, bending, lifting, twisting, reaching, and transitioning from one position to another.

EXAMPLE 1

Assessment. The condition of a patient with a shoulder pain and movement impairments was assessed. The patient's medical diagnosis included shoulder impingement, rotator cuff strains, chronic bursitis, shoulder tendinosis, frozen shoulder, shoulder sprain (stretch or tear in a ligament), or shoulder strain (stretch or tear in muscles or tendon). The patient suffered from a constant pain with or without shoulder movements. The patient's pain increased at the end range of shoulder movements. The patient self-evaluated the shoulder pain level as being between 3 and 6 out of 10. The patient movement restrictions and/or loss included shoulder flexion (moving arms anywhere from a resting position by sides to straight above head), abduction (lifting arm out to the side), external and internal rotation (rotating the arm so that the elbow faces backward or forward respectively), horizontal adduction (lifting arm out to the side and moving it to the front), and horizontal abduction (lifting the arm in the front and moving it to the side). These restrictions interfered with daily living activities of the patient including putting on or taking off clothing independently, reaching overhead, sleeping, and performance of hygiene tasks. The patient avoided sport and other recreational activities owing to these pain and mobility restrictions.

Treatment. The patient with a shoulder pain, shoulder and arm movement impairments was treated by performing tissue reconfiguration therapy using domes in combination with suitable passive and active arm movement and stretching exercises. The following steps were performed to reconfigure the patient's affected/injured shoulder tissue and facilitate pain relief and movement restrictions:

1. The patient's pain level prior to the therapy session was assessed and recorded. The assessment comprised having the patient complete a standard written form questionnaire to assess the levels of pain and the specific movement restrictions experienced. The questionnaire included various questions to quantify the degree of the pain generally experienced during the performance of certain tasks and movements. The patient was required to assign a numerical value between 0 and 10 to indicate the degree of pain experienced (zero where there was no pain and/or impairment). Information obtained from the questionnaire was supplemented by interviewing the patient to further describe and determine the intensity/degree of pain and impairment associated with various specific movements and/or tasks.
2. A specific movement was selected from those causing a maximum degree of pain as found in step 1. This was found to be a right-side shoulder and arm movement.
3. The patient laid on an exam table face up (supine), face down (prone), or on a side position (left lateral recumbent) depending on the shoulder muscle injured and the movement restrictions.
4. The active and passive ranges of motion in the patient's right shoulder and arm were observed and measured according to standard guidelines for joint motion measurement (Measurement of Joint Motion: A Guide to Goniometry, Cynthia C. Norkin and D. Joyce White, 2016, F. A. Davis Company). Typically, potential ranges of shoulder movements with minimum and maximum values include shoulder flexion (0 to 180°), shoulder extension (0 to 50°), shoulder abduction (0 to 90°), shoulder adduction (90 to 0°), medial rotation (0 to 90°), and lateral rotation (0 to 90°). The patient's measured movements were compared to characteristic ranges found in healthy individuals. The level of the patient's pain associated with performing these movements was recorded.

5. The patient's right shoulder muscle (for example anterior deltoid and supraspinatus) strength at the end point in active range was measured using a stress gauge or standard manual muscle test procedures (Muscles Testing and Function with Posture and Pain, Florence Peterson Kendall, Elizabeth Kendall McCreary, Patricia Geise Provance, Mary Mcintyre Rodgers, William Romani, 2005, Lippincott Williams & Wilkins).
6. The patient's shoulder muscle trigger point and the area of shoulder joint (glenohumeral) restriction were located following these steps below. 1) First the patient's right shoulder muscles including anterior deltoid, supraspinatus, bicep long head, and others were examined to identify the specific shoulder muscle that restricted the movement and caused pain 2) Then the center of the pain causing shoulder muscle belly was identified and pressed transversely to the fibers to assess tenderness, stiffness, pliability, and transient asynchronous muscle contractions. At the trigger point, the tissue is generally tender and elicits pain when touched. The muscles might also have transient asynchronous contractions at the resting state. 3) Lastly an area of a joint restriction was located by passively moving patient's joint to and away from the restriction and placing finger tips over a muscle area that did not move.
7. A suitable size and shape dome was chosen to cover an approximate area of an identified trigger point and the joint restriction causing the pain and movement impairment.
8. The dome was placed over the identified trigger point and/or joint restriction on the patient's affected shoulder while patient right arm was at a position where the patient has the maximum pain and a predetermined subatmospheric pressure was applied to the dome using a vacuum pump sealingly connected to the dome through a vacuum manifold as disclosed herein. The pressure in the dome was maintained for a preselected time interval, generally 15-60 seconds.
9. The patient's right arm was passively stretched into the end point of restriction gradually by the physical therapist according to the patient's tolerance of pain.
10. The patient was asked to lift right arm against the gravity as high as possible then isometrically hold this position for 3 seconds. The tissue reconfiguration therapy using domes with passive arm movements and stretching at step 9 was repeated three times.
11. The dome from the patient's right shoulder was released by lifting the check valve on the top of the dome and allowing air into the dome and repositioned on the affected tissue area adjacent to the previous position of the dome, including the trigger point identified.
12. The tenderness, stiffness, any contractions of the patient's right shoulder tissue at resting state were re-examined and compared with those recorded at the beginning of the therapy session.
13. The end ranges of patient's right shoulder and arm motions were re-measured to monitor the outcome of the tissue reconfiguration therapy using domes in combination with the stretching exercise.
14. The steps from 8 to 11 were repeated several times depending on the size and degree of stiffness of the patient's affected tissue.
15. If the patient had more than one movement elements that caused pain, the steps from 1 to 14 were repeated for each specific movement restriction of the patient to facilitate the recovery further.

EXAMPLE 2

Assessment. The condition of a patient with a neck and back pain and movement impairments was assessed. The patient's medical diagnosis included cervicalgia (neck pain), cervical strain (neck pain due to overstretching of muscles or tendons in the neck), cervical sprain (neck pain due to overstretching of ligaments in the neck), fibromyalgia (musculoskeletal pain), cervical radiculitis (inflamed or damage nerve root in the cervical spine), cervical stenosis (damage to the spinal cord and nerve roots because of reduced space/volume of the spinal canal), cervical degenerative disc disease (neck pain due to break down of the cushioning discs in the cervical spine), facet syndrome (loss or reduced coating of the capsule and the cartilage in the neck or lower back joints of vertebrae), thoracic strain/sprain (thoracic muscle or tendon injury/thoracic ligament injury), abnormal posture, dowagers hump (hump of spine due to forward bending of the spine), thoracic stenosis, and costochondritis (inflammation of the cartilage). The patient suffered from a constant pain with or without neck movements. The patient's pain increased at the end range of his neck movements. The patient self-evaluated the neck pain level as being between 3 and 6 out of 10. The patient movement restrictions and loss included neck flexion (a neck movement where the chin is lowered toward the chest), extension (a neck movement where the neck is extended to look upward toward the ceiling), abduction, and rotation (lateral rotation to the left or right). These restrictions interfered with daily living activities including putting on or taking off clothing independently, reaching overhead, sleeping, and performance of hygiene tasks, and driving. Moreover, the patient could not exercise and play sport and/or perform other recreational activities owing to these pain and mobility restrictions.

Treatment. The patient with upper back pain, neck pain and tension in neck and upper back and movement impairments was treated by performing tissue reconfiguration therapy using domes in combination with relevant stretching exercises as disclosed herein. The following steps were performed:

1. A numerical assessment of pain level prior to the therapy session was made and recorded. The assessment comprised having the patient complete a standard written form questionnaire to assess the levels of pain and the specific movement restrictions experienced. The questionnaire included various questions operable to quantify the degree of the pain generally experienced during the performance of certain tasks and movements. The patient was required to assign a numerical value between 0 and 10 to indicate the degree of pain experienced (zero where there was no pain and/or impairment). Information obtained from the questionnaire was supplemented by interviewing the patient to further describe and determine the intensity/degree of pain and impairment associated with various specific movements and/or tasks.

2. A specific movement was selected from those causing a maximum degree of pain as found in step 1. This was found to be neck movements.
3. The patient laid on an exam table face up (supine), face down (prone), or on a side position (right or left lateral recumbent) depending on the types of the neck muscle and the movement restrictions.
4. The active and passive ranges of motion in patient's neck and both shoulders were measured according to the standard protocols (Measurement of Joint Motion: A Guide to Goniometry, Cynthia C. Norkin and D. Joyce White, 2016, F. A. Davis Company, hereby incorporated by references in its entirety for all purposes). Typical ranges of neck movements relative to the neural neck position indicating minimum and maximum values (the head balances directly above spine and not lean forward, backward or sides) include neck flexion (0 to 38°), extension (0 to 38°), abduction and rotation (0 to 45°). The patient had 20° neck flexion, 23° neck extension, and 30° neck rotation, which were less than the typical maximum ranges of the neck movements described above. One of patient's neck and/or back movements that caused the maximum pain was selected. The degree of patient's movement restrictions and the associated pain for each movement restriction was quantified according to the standard guidelines thoroughly.
5. The patient's neck muscle trigger point and the patient's area of joint restriction were located following these steps: 1) First the patient's neck muscle causing pain and limiting the movements was determined. 2) Then the center of the muscle belly causing neck pain was found and pressed transversely to the fibers to assess the tenderness, stiffness, pliability, and any transient asynchronous muscle contractions. At the trigger point, the tissue is generally tender and elicits pain when touched. The muscles may also have transient asynchronous contractions at the resting state. 3) An area of a joint restriction was located by passively moving patient's joint to and away from the restriction and placing fingertips over a muscle area that did not move.
6. A suitable size and shape dome was chosen to cover an approximate area of an identified trigger point and the joint restriction causing the pain at patient's neck.
7. The domes were placed over the trigger points and joint restriction on patient's neck region while patient's neck and arm in a position where the patient felt the maximum pain. And a predetermined subatmospheric pressure was applied sealingly to these domes and maintained for a preselected time interval using a vacuum pump sealingly connected to these domes through a vacuum manifold as disclosed herein.
8. The patient was asked to lift arms against gravity as high as possible then isometrically hold this position for 3 seconds. The passive stretching in combination with the dome therapy at step 7 were repeated three times.
9. The dome was released from the patient's neck and upper back by lifting the check valve on the top of the dome and allowing air into the dome and repositioned adjacent to the previously treated area of tissue using the dome, including the trigger point.
10. The tenderness, stiffness, any muscle contractions (at resting state) at the patient's neck and upper back tissue were re-examined after the therapy and compared with previous measurements at the beginning of the therapy session.
11. The end ranges of patient's specific neck and arm movements were re-measured to monitor the effect of the tissue reconfiguration therapy using domes in combination with stretching exercise.
12. The patient had more than one neck and back movement restrictions that caused pain, the steps from 1 to 11 were repeated for each specific movement of the patient to facilitate the recovery further.

EXAMPLE 3

Assessment. The condition of a patient with a lower back and hip pain and tension with movement impairments was assessed. The patient's medical diagnosis included lumbago (pain in the muscles and joints of lower back), lumbar strain/sprain (stretching injury to the muscles, tendons and ligaments of the lower back), fibromyalgia (musculoskeletal pain), lumbar radiculitis (injured, pinched, or compressed nerves in lower back), lumbar stenosis (damage to nerves relaying information from lower back to the legs because of narrowing of the spinal canal), lumbar degenerative disc disease (loss of cushioning between spinal discs, fragmentation or herniation of the spinal discs in the lower back), lumbar facet syndrome (a dysfunction at the posterior facet joints of the spine), spondylosis (a crack or stress fracture in one of the vertebrae), hip strain/sprain (an overstretch or torn of muscles, tendons or ligaments around the hip), and chronic hip bursitis (inflammation and irritation of one or more of the bursae in hip due to repetitive motions or positions). The patient suffered from a constant pain with or without back movements. The patient pain increased at the end range of back movements. The patient self-evaluates the back-pain level as being between 3 and 6 out of 10. The patient's movement restrictions and pain affected the patient's ability to perform back flexion (bending the spine forward from the waist), extension (bending the spine backward), abduction (movement of a body away from the center of the body), and rotation (rotation of the thigh or leg toward or away from the center of the body). These restrictions interfered with daily living activities including putting on or taking off clothing independently, reaching overhead, sleeping, and performance of hygiene tasks, driving, and lifting and carrying objects. The patient was unable to exercise and perform other recreational activities owing to these pain and mobility restrictions.

Treatment. The patient with a lower back and hip pain and tension with movement impairments was treated by performing tissue reconfiguration therapy using domes in combination with relevant stretching exercise as disclosed herein. The following steps were performed:

1. A numerical assessment of pain level prior to the therapy session was made and recorded. The assessment comprised having the patient complete a standard written form questionnaire to assess the levels of pain and the specific movement restrictions experienced. The questionnaire included various questions operable to quantify the degree of the pain generally experienced during the performance of certain tasks and movements. The patient was required to assign a numerical value between 0 and 10 to indicate the degree of pain experienced (zero where there was no pain and/or impairment). Information obtained from the questionnaire was supplemented by interviewing the patient to further describe and determine the intensity/degree of pain and impairment associated with various specific movements and/or tasks.

2. A specific movement was selected from those causing a maximum degree of pain as found in step 1. This was found to be back movements.
3. The patient laid on an exam table face down (prone), or on a side position (right or left lateral recumbent) to apply therapy for the back pain and hip pain and restrictions depending on the position of the injured tissue.
4. The active and passive ranges of motion in the patient's back and both hips were measured according to the standard protocols (Measurement of Joint Motion: A Guide to Goniometry, Cynthia C. Norkin and D. Joyce White, 2016, F. A. Davis Company, hereby incorporated by references in its entirety for all purposes). Typical ranges of hip movements with minimum and maximum values include flexion (0 to 125°), extension (115 to 0°), hyperextension (straightening beyond normal range, 0 to 15°), abduction (0 to 45°), adduction (45 to 0°), lateral/external rotation (rotation away from the center of body, 0 to 45°), medial/internal rotation (rotation toward the center of body, 0 to 45°). The patient's movements that caused the maximum pain were selected and the degree of the patient's movement restrictions and associated pain were quantified as compared to the standard controls in normal individuals.
5. The patient's back and hip muscle trigger points and area of joint restriction were located following these steps: 1) The patient's specific back muscle and hip muscle causing pain and limiting the movements was determined. 2) The center of patient's back or hip muscle belly causing pain was found and pressed transversely to the fibers to assess the tenderness, stiffness, pliability, and transient asynchronous muscle contractions. At the trigger point, the tissue is generally tender and elicits pain when touched. The muscles may also have transient asynchronous contractions at the resting state. 3) Then an area of a joint restriction was located by passively moving the patient's joint to and away from the restriction and placing fingertips over a muscle area that did not move.
6. The domes were placed over the center of the identified trigger points on the patient's back (for example multifidus muscle) while the patient was in a position that made the patient feel the maximum pain. And a predetermined subatmospheric pressure was applied to the dome using vacuum pump sealingly connected to the dome through a vacuum manifold as disclosed herein and maintained for a preselected time interval.
7. The patient was asked to lift legs against gravity off the table approximately one inch (if able) then isometrically hold this position for 3 seconds. These active and passive stretching exercises in combination with the dome therapy was repeated three times.
8. The dome was released from the patient's back by lifting the check valve on the top of the dome and allowing air into the dome and repositioned on the patient's affected back region adjacent the previous position of the dome, including the identified trigger point.
9. The passive stretching in combination with the dome therapy was repeated three times by repositioning the dome distally to the center of trigger point with an approximate 15% overlap with the previous dome position on patient's back.
10. The dome was released from the patient's back according to the method disclosed herein.
11. The tenderness, stiffness, any muscle contractions (at resting state) at the patient's back tissue was examined and compared with those of his back prior to the therapy session.
12. The ranges of patient's back movements were remeasured to monitor the effect of the tissue reconfiguration therapy using domes in combination with suitable stretching exercise.
13. The domes were placed over the center of the identified trigger points on the patient's hip (for example tensor fascia latae muscle, piriformus muscle, and glut muscles) while patient hip was in position where the patient felt the maximum pain. And a predetermined subatmospheric pressure was applied to the dome using vacuum pump sealingly connected to the dome through a vacuum manifold as disclosed herein and maintained for a preselected time interval.
14. The patient was asked to lift legs against gravity off the table approximately one inch (if able) then isometrically hold this position for 3 seconds. The patient's affected leg was bent and moved toward and away from the center of the body by the therapist during the tissue reconfiguration therapy using domes. These active and passive stretching exercises in combination with the dome therapy was repeated three times.
15. The dome was released from the patient's hip tissue by lifting the check valve on the top of the dome and allowing air into the dome and repositioned on the patient's affected hip region adjacent the previous position of the dome, including the identified trigger point.
16. The tenderness, stiffness, any muscle contractions at resting state at the patient hip tissue were examined and compared with those of the patient's hip tissue prior to the therapy session.
17. The ranges of patient's hip movements were remeasured to monitor the effect of the tissue reconfiguration therapy using dome in combination with the stretching exercise.
18. The patient had additional movement restrictions that caused pain, the steps 1 to 12 for each specific movement were performed to improve the recovery further.

EXAMPLE 4

Assessment. The condition of a patient having a shin splint at right lower leg was accessed. The patient ran 20 to 25 miles per week. The patient was a mid-foot runner with a lot of up and down movement elements but recently modified running style to less up and down movements. The patient's medical diagnosis included shin splints with tenderness and swelling located at 8 to 4 cm posterior medial distal to mid shaft of the tibia at origin posterior tibialis associated with pain. The patient's pain was exacerbated after running. The patient had a limitation of bilateral hip and back extension. These limitations in the hip and back caused an excessive dorsiflexion with every step resulting in overuse in the muscles of the leg and ankle area.

Treatment. The patient having a shin splint at his right lower leg was treated by performing tissue reconfiguration therapy using domes disclosed herein in combination with relevant stretching, and breathing exercises in order to relax the tight soft tissues involved in running activity particularly the muscles in lower and upper legs, flexors, hip and back.

1. The patient was positioned for the session. He was asked to assume a typical runners' calf stretch position (Yoga For Runners, Christine Felstead, 2014, Human Kinetics, hereby incorporated by references in its entirety for all purposes).
2. The patient's hip and back extension in standing position were measured using the standard goniometric assessment guidelines (Measurement of Joint Motion: A Guide to Goniometry, Cynthia C. Norkin and D. Joyce White, 2016, F. A. Davis Company, hereby incorporated by references in its entirety for all purposes). Typically ranges of hip, back and knee movements include hip extension (0 to 20°), back extension (0 to 25°), range of knee movements include knee flexion (0 to 130°), knee extension (120 to 0°), and ranges of ankle movements include plantar flexion (movement downward, 0 to 50°) and dorsiflexion (movement upward, 0 to 20°). Then the patient was asked to evaluate the level of pain in leg and shin using a standard numerical pain scale between 0 to 10 (zero where there was no pain and/or impairment).
3. Three domes were placed over the patient's tight calf muscle on lower right leg and an atmospheric pressure of 0.75 atm was applied to these domes and maintained for a preselected time interval using a vacuum pump sealingly connected to the dome through a vacuum manifold as disclosed herein.
4. Three domes were placed over the front of the patient tight thigh muscles including muscles tensor fascia latae, and rectus femoris. A subatmospheric pressure of 0.75 atm was applied and maintained for a predetermined time interval using a vacuum pump sealingly connected to the dome through a vacuum manifold as disclosed herein.
5. Two additional domes were placed at the lower back of the patient over the area called multifidus. A subatmospheric pressure of 0.75 atm was applied and maintained the domes over the identified trigger points at the patient's lower back for a predetermined time interval using a vacuum pump sealingly connected to the dome through a vacuum manifold as disclosed herein.
6. The patient was asked to stretch right leg as much as possible and hold in this stretching position for 3 seconds. Then the patient was asked to take a breath while going into the stretching position and breath out while holding the stretching position. The patient was asked to repeat the stretching and breathing exercises three times.
7. The domes were released according to the method disclosed herein and repositioned over the patient's additional tight muscle regions on the right lower leg, thigh, and lower back muscles. A subatmospheric pressure was applied and maintained as described previously.
8. The patient was asked to repeat the stretching and breathing exercises as above.
9. The tightness, stiffness, and any muscle contraction on the patient's right lower leg, thigh, and lower back were re-examined by palpation method. The domes were repositioned over the additional patient's tight muscles of the right lower leg, thigh, and lower back. The steps of application of the tissue reconfiguration therapy using domes were followed. The stretching and breathing exercises with the repositioned domes were incorporated as described above.
10. The tightness and stiffness of the patient's left hip and back muscles involved in running were also accessed. The patient's left hip and back extension were remeasured according to the standard goniometer protocols to monitor the functional recovery of the patient after the therapy session. The limitations in his left hip and back extension and pain, are also treated as described for the patient's right leg.

EXAMPLE 5

Assessment. The condition of a patient with hand and finger pain and movement impairments was assessed. The patient's medical diagnosis included pain in left hand soft tissue, stiffness of left hand, weakness, and abnormal posture. The patient suffered from a constant pain when using left hand has restrictions in left hand finger movements. Patient pain increased at the end range of finger movements. The patient self-evaluated the hand pain level as being between 3 and 6 out of 10. The patient hand and finger movement restrictions included finger flexion (moving the base of the finger toward the palm), extension (moving the base of the fingers away from the palm), abduction (moving the fingers away from the middle finger), adduction (moving the fingers toward the middle finger), abduction (moving the fingers away from the middle finger), opposition (ability to bring the tip of a thumb in contact with a tip of a finger) and reposition (moving the thumb away from the finger to the neural hand position). These limitations in the patient's hand movements caused difficulties in daily living activities such as putting on or taking off clothing independently, and performance of hygiene tasks, and others.

Treatment. The patient with a hand pain, hand and finger movement impairments was treated by performing tissue reconfiguration therapy using domes in combination with passive and active stretching exercises. The following steps were performed to reconfigure the soft tissue in the patient's affected/injured hand and facilitate pain relief and finger movement restrictions:

1. The patient's pain level prior to the therapy session was assessed and recorded. The assessment comprises having the patient complete a standard written form questionnaire to assess the levels of pain and the specific movement restrictions experienced. The questionnaire included various questions to quantify the degree of the pain generally experienced during the performance of certain tasks and movements. The patient was required to assign a numerical value between 0 and 10 to indicate the degree of pain experienced (zero where there was no pain and/or impairment). Information obtained from the questionnaire was supplemented by interviewing the patient to further describe and determine the intensity/degree of pain and impairment associated with various specific movements and/or tasks.
2. A specific movement was selected from those causing a maximum degree of hand pain as found in step 1. This was found to be movements of the patient's index finger due to an injury.
3. The patient laid on an exam table face up (supine).
4. The active and passive ranges of motion in patient's hand and fingers were measured according to the standard protocols (Measurement of Joint Motion: A Guide to Goniometry, Cynthia C. Norkin and D. Joyce White, 2016, F. A. Davis Company). Typically ranges of finger movements relative to the neural finger position include flexion (moving the base of the finger towards the palm, 0 to 90° for metacarpophalangeal joints of the finger, 0 to 120° for interphalangeal proximal joints of the finger, 0 to 80° for interphalangeal distal joints of the finger, 0 to 70° for 0 to 30° for metacarpophalangeal joints of the finger thumb), extension (moving the base of the fingers away from the palm, 0 to 30° for metacarpophalangeal joints of the finger, 120 to 0° for interphalangeal proximal joints of the finger, 80 to 0° for interphalangeal distal joints of the finger, 60 to 0° for metacarpophalangeal joints of thumb), abduction (moving the finger away from the middle finger, 0 to 25° for metacarpophalangeal joints of the finger, 0 to 50° for metacarpophalangeal joint of thumb), adduction (moving the finger toward middle finger, 20 to 0° for metacarpophalangeal joints of the finger, 40 to 0° for metacarpophalangeal joint of thumb). One of patient's hand and finger movements that caused the maximum pain was selected. The degree of patient's movement restrictions and the associated pain for each movement restriction was quantified according to the standard guidelines thoroughly.

6. The patient's hand muscle trigger point and area of joint restriction were located following these steps: 1) First the patient's hand muscle causing pain and limiting the movements was determined. 2) Then the center of the hand muscle belly causing pain was found and pressed transversely to the fibers to assess the tenderness, stiffness, pliability, and any transient asynchronous muscle contractions. At the trigger point, the tissue is generally tender and elicits pain when touched. The muscles may also have transient asynchronous contractions at the resting state. 3) An area of a joint restriction was located by passively moving patient's joint to and away from the restriction and placing fingertips over a muscle area that did not move.
7. A suitable size and shape dome (3.5 in or 4.5 in inner diameter dome with curved edge bottom) was chosen to cover an approximate area of the identified trigger point and the joint restriction causing the pain at patient's hand.
8. The dome was placed over the trigger point and joint restriction on dorsal side of patient's hand region near the affected finger while the patient's hand and finger in a position where the patient felt the maximum pain. And a predetermined subatmospheric pressure was applied to the dome using a vacuum pump sealingly connected to the dome through a vacuum manifold as disclosed herein and maintained for a preselected time interval, usually 15-60 seconds.
9. The patient was asked to bend the affected finger as much as possible then hold this position for 3 seconds. The active and therapist assisted passive stretching of the affected finger in combination with the tissue reconfiguration therapy using domes at step 8 were repeated three times.
10. The domes were released from the patient's hand and upper back by lifting the check valve on the top of each dome and allowing air into each dome and repositioned on the patient's hand and upper back region adjacent the previous position of the domes, including the identified trigger points. Steps 8 to 10 were repeated till all the trigger point area was covered.
11. A dome (3.5 in inner diameter with curved edge bottom) was placed over the trigger point on ventral side of patient's hand region near the affected finger while the patient's hand and finger in a position where the patient feels the maximum pain. And a predetermined subatmospheric pressure was applied to the dome using a vacuum pump sealingly connected to the dome through a vacuum manifold as disclosed herein and maintained for a preselected time interval, usually 15-60 seconds.
12. The patient was asked to push the affected hand and finger against the force that the physical therapist applies, hold this position for 3 seconds, and relax during the tissue reconfiguration therapy using domes. This active and passive stretching exercises of the affected finger in combination with the tissue reconfiguration therapy using domes at step 7 were repeated three times.
13. The dome is released from the ventral side of the patient's hand by lifting the check valve on the top of the dome and allowing air into the dome and repositioned on the patient's affected hand region adjacent the previous position of the dome, including the identified trigger point. Steps 11 to 13 were repeated till the trigger point area was covered.
14. A dome (1.8 in inner diameter with curved edge bottom) was placed near and around the finger joint of patient's affected finger (while patient's finger in a position where the patient felt the maximum pain. And a predetermined subatmospheric pressure was applied to the dome using a vacuum pump sealingly connected to the dome through a vacuum manifold as disclosed herein and maintained for a preselected time interval, usually 15-60 seconds.
15. The patient was asked to push the affected hand and finger against the force that the physical therapist applied, hold this position for 3 seconds, and relax during the tissue reconfiguration therapy using domes. This active and passive stretching exercises of the affected finger in combination with the tissue reconfiguration therapy using domes therapy at step 8 were repeated three times.
16. The dome was released from the finger joint of the patient's hand by lifting the check valve on the top of the dome and allowing air into the dome.
17. The tenderness, stiffness, any muscle contractions at the patient's hand and finger tissue at resting state were re-examined after the therapy and compared with the measurements at the beginning of the therapy session.
18. The end ranges of patient's specific finger movements were re-measured to monitor the effect of the tissue reconfiguration therapy using domes in combination with stretching exercise.
19. After the tissue reconfiguration therapy using domes was completed, the patient's affected finger was massaged gently using Graston™ GT6 to facilitate the recovery further.
20. The tenderness and stiffness of the patient's affected finger tissue at resting state were re-examined after the massage therapy and compared with the measurements at the beginning of the therapy session.
21. The end ranges of patient's specific finger movements were re-measured to monitor the effect of the tissue reconfiguration therapy using domes in combination with suitable stretching exercises and the massage therapy.
22. The patient had also wrist movement restrictions that causes pain, particularly during the wrist extension movement.
23. A dome (4.5 in inner diameter with curved edge bottom) was placed over the trigger point on ventral side of patient's hand near the affected wrist while patient's wrist in a position where the patient feels the maximum pain. And a predetermined subatmospheric pressure was applied to the dome using a vacuum pump sealingly connected to the dome through a vacuum manifold as disclosed herein and maintained for a preselected time interval, usually 15-60 seconds.

24. The patient was asked to push the affected hand and finger against the force that the physical therapist applied, hold this position for 3 seconds, and relax during the tissue reconfiguration therapy using domes. This active and passive stretching exercises of the affected wrist in combination with the tissue reconfiguration therapy using domes at step 23 were repeated three times.
25. The dome was released from the ventral side of the patient's hand by lifting the check valve on the top of the dome and allowing air into the dome and repositioned over the arm near the affected wrist. Steps 22 to 24 were repeated.
26. A dome (6 in inner diameter with curved edge bottom) was placed over the patient's arm near the affected wrist proximal to the region the previously reconfigured tissue including the identified trigger point while the patient's wrist in a position that caused the patient the maximum pain. And a predetermined subatmospheric pressure was applied to the dome using a vacuum pump sealingly connected to the dome through a vacuum manifold as disclosed herein and maintained for a preselected time interval, usually 15-60 seconds.
27. The patient was asked to push the affected wrist against the force that the physical therapist applied, held this position for 3 seconds, and relaxed during the tissue reconfiguration therapy using domes. This active and passive stretching exercises of the affected wrist in combination with the tissue reconfiguration therapy using domes at step 26 were repeated three times.
28. The dome was released from the patient's arm by lifting the check valve on the top of the dome and allowing air into the dome.
29. The tenderness and stiffness of the patient's affected wrist tissue at resting state were re-examined after the therapy and compared with the measurements at the beginning of the therapy session.
30. The end ranges of patient's specific wrist movements were re-measured to monitor the effect of the tissue reconfiguration therapy using domes in combination with stretching exercises and the massage therapy.
31. The patient right and left-hand strength was measured using dynameter.

EXAMPLE 6

Assessment. The condition of a patient with right foot pain and movement impairments was assessed. The patient's medical diagnosis included plantar fasciitis, Achilles tendinitis, stiffness of right leg, and difficulty of walking. The patient suffered from a constant foot pain at the bottom and sides with and without movements. The patient's pain increased as the patient stands up and walks. The patient self-evaluated the foot pain level as being between 3 and 6 out of 10. Patient movement restrictions and loss also included hip abduction (lifting left out to the side), and internal hip rotation (twisting movement of thigh inward from the hip joint). These restrictions interfered with the patient's daily living and recreational activities, and performance of exercises.

Treatment. The patient with a foot pain, leg and hip movement impairments was treated by performing a tissue reconfiguration therapy using domes in combination with passive and active foot and leg stretching exercises. The following steps were performed to reconfigure the patient's affected/injured tissue and facilitate pain relief and movement restrictions:

1. The patient's pain level prior to the therapy session was assessed and recorded. The assessment comprised having the patient complete a standard written form questionnaire to assess the levels of pain and the specific movement restrictions experienced. The questionnaire included various questions to quantify the degree of the pain generally experienced during the performance of certain tasks and movements. The patient was required to assign a numerical value between 0 and 10 to indicate the degree of pain experienced (zero where there was no pain and/or impairment). Information obtained from the questionnaire was supplemented by interviewing the patient to further describe and determine the intensity/degree of pain and impairment associated with various specific movements and/or tasks.
2. A specific movement was selected from those causing a maximum degree of pain as found in step 1. This was found to be the heel of the patient' right foot and right leg movements.
3. The patient laid on an exam table face up (supine), face down (prone), or on a side position (left lateral recumbent) depending on the position of the muscle being treated.
4. The active and passive ranges of motion in the patient's right feet were observed and measured according to standard guidelines for joint motion measurement (Measurement of Joint Motion: A Guide to Goniometry, Cynthia C. Norkin and D. Joyce White, 2016, F. A. Davis Company). Typical ranges of foot movements include inversion (rolling foot inward, from 0 to 35°), eversion (rolling foot outward about from 0 to 25°), ranges of ankle include plantar flexion (moving the tip of foot downward, 0 to 50°), dorsiflexion (moving the tip of foot upward, 0 to 20°), and typical ranges of hip movements include flexion (raising the leg toward front, 0 to 125°), extension (returning the flexed leg toward neutral leg position, 115 to 0°), hyperextension (hip joints extend forward while pelvis moves forward and back leans backward, 0 to 15°), abduction (moving the thigh away from the midline of the body, 0 to 45°), adduction (45 to 0°, moving the thigh closer to the midline of the body), lateral movement (moving the thigh away from the midline of the body laterally, 0 to 45°), medial rotation (rotation toward the center of the body, 0 to 45°). The measured movements were compared to characteristic ranges found in normal individuals. The patient's hip abduction and internal rotation movements were impaired completely. The level of pain associated with performing these movements was recorded.
6. The patient laid on the exam table facing up with a pillow under the right leg to raise the foot level such that the bottom of the foot can be held and treated easily. The patient's right foot muscle (abductor digiti minimi muscle, adductor hallucis transverse muscle, adductor hallucis, oblique muscle, flexor hallucis brevis, medial and lateral heads) strength at end point in active range was measured using a stress gauge or standard manual muscle test procedures (Muscles Testing and Function with Posture and Pain, Florence Peterson Kendall, Elizabeth Kendall McCreary, Patricia Geise Provance, Mary Mcintyre Rodgers, William Romani, 2005, Lippincott Williams & Wilkins).

7. The patient's foot muscle trigger point and an area of foot joint restriction were located following these steps below. 1) First the patient's right foot muscles including abductor digiti minimi muscle, adductor hallucis transverse muscle, adductor hallucis, oblique muscle, flexor hallucis brevis, medial and lateral heads were examined to identify the specific foot muscle that restricted the movement and caused pain 2) Then the center of the pain causing foot muscle belly was identified and pressed transversely to the fibers to assess tenderness, stiffness, pliability, and transient asynchronous muscle contractions. At the trigger point, the tissue is generally tender and elicits pain when touched. The muscles may also have transient asynchronous contractions at the resting state. 3) Lastly the area of a joint restriction was located by passively moving patient's joint to and away from the restriction and placing finger tips over a muscle were a that does not move.
8. A suitable size and shape dome (usually 4.5 in inner diameter with a curved bottom edge dome to accommodate the curvature of the foot) were chosen to cover an approximate area of the identified trigger point and the joint restriction causing the pain and movement impairment.
9. The dome was placed over the identified trigger point and joint restriction on the patient's affected foot pad.
10. A predetermined subatmospheric pressure was applied to the dome using a vacuum pump sealingly connected to the dome through a vacuum manifold as disclosed herein while the patient right foot was at a position where the patient has the maximum pain. And the pressure was maintained for a preselected time interval, generally 15-60 seconds.
11. The patient's right foot was passively stretched into the end point of restrictions for dorsiflexion and plantar flexion movements gradually by the physical therapist according to the patient's tolerance of pain.
12. The patient pushes the tip of the right foot forward (plantar flexion movement) as much as possible, isometrically holds this position for 3 seconds, and relaxes the foot. The tissue reconfiguration therapy using domes with these passive and active foot stretching at steps 10 to 12 was repeated three times.
13. The dome at the patient's right foot pad was released by lifting the check valve on the top of the dome and allowing air into the dome.
14. The dome was repositioned near lateral region of the patient's right foot heel including another trigger point. And the steps from 11 to 14 were repeated.
15. The dome was repositioned near medial region of the patient's right foot heel covering another trigger point. And the steps from 11 to 14 were repeated.
16. A massage to the bottom of the patient's right foot was applied using Graston™ GT3 tool.
17. The tenderness and stiffness of the patient's right foot tissue at resting state were re-examined and compared with those recorded at the beginning of the therapy session.
18. The end ranges of the patient's right foot and ankle movements were re-measured to monitor the outcome of the tissue reconfiguration therapy using dome s in combination with the stretching exercises.
19. The patient has also Achilles tendinitis and stiffness at right lower leg. The trigger points of the patient lower right leg were determined as described at step 8.
20. The dome was placed over the identified trigger point and joint restriction on the patient's affected lower leg.
21. A predetermined subatmospheric pressure was applied to the dome using a vacuum pump sealingly connected to the dome through a vacuum manifold as disclosed herein while the patient right leg was at a position where the patient had the maximum pain. And the pressure was maintained for a preselected time interval, generally 15-60 seconds.
22. The patient's right foot was passively stretched into the end point of restrictions the physical therapist bent and moved the patient's right foot to simulate dorsiflexion and plantar flexion movements gradually by according to the patient's tolerance of pain.
23. The patient pushed the tip of the right foot forward (plantar flexion movement) as much as possible, isometrically held at this position for 3 seconds, and relaxed the foot. The tissue reconfiguration therapy using domes with these passive and active foot stretching at steps 21 to 23 was repeated three times.
24. The dome at the patient's right leg was released by lifting the check valve on the top of the dome and allowing air into the dome.
25. A dome (5 in in inner diameter with flat edge) was repositioned over a trigger point in the patient's calf muscles of the right lower leg. And the steps from 22 to 25 were repeated.
26. Depending on the degree of stiffness of the patient's lower leg muscles, multiple dome s (generally 5 in in inner diameter with flat edge) were positioned over the identified trigger points of the patient's lower leg muscles including calf muscle and the steps from 22 to 25 were repeated.
27. A dome was repositioned over a trigger point on the patient's calf muscles of the right lower leg near the knee. And the steps from 11 to 14 were repeated.
28. The patient has more than one movement elements that caused pain, the steps from 1 to 14 were repeated for each specific movement of the patient to facilitate the recovery further.

EXAMPLE 7

Assessment. The condition of a patient with neck and arm pain and right arm and wrist movement impairments was assessed. The patient's medical diagnosis included unspecified injury of muscle, fascia and tendon of long head of biceps, left arm, initial encounter, strain of muscle, fascia and tendon of other parts of biceps, left arm, initial encounter, abnormal posture, cervicalgia, benign parxymal vertigo. The patient suffered from a constant pain radiating all the way down the arm, and movement restrictions in the arm. Patient pain increases as the right arm was extended. The patient self-evaluated the hand pain level as being between 3 and 6 out of 10. The patient's arm movement restrictions affect included wrist flexion (bending the palm down toward the wrist) and extension (bending the palm up away from the wrist). These limitations in the patient's neck pain and movement restrictions caused difficulties in daily living activities such as putting on or taking off clothing independently, and performance of hygiene tasks, and others.

Treatment. The patient with a neck pain, right arm and wrist movement impairments was treated by performing a tissue reconfiguration therapy using domes in combination with passive and active arm and wrist stretching exercises. The following steps were performed to reconfigure the soft tissue in the patient's affected arm and facilitate pain relief and movement restrictions:

1. The patient's pain level prior to the therapy session was assessed and recorded. The assessment comprises having the patient complete a standard written form questionnaire to assess the levels of pain and the specific movement restrictions experienced. The questionnaire includes various questions to quantify the degree of the pain generally experienced during the performance of certain tasks and movements. The patient was required to assign a numerical value between 0 and 10 to indicate the degree of pain experienced (zero where there was no pain and/or impairment). Information obtained from the questionnaire was supplemented by interviewing the patient to further describe and determine the intensity/degree of pain and impairment associated with various specific movements and/or tasks.
2. A specific movement was selected from those causing a maximum degree of pain as found in step 1. This was found to be the extension of the patient's right arm.
3. The patient lays on an exam table face up (supine).
4. The active and passive ranges of motion in patient's arm and wrist were measured according to the standard protocols (Measurement of Joint Motion: A Guide to Goniometry, Cynthia C. Norkin and D. Joyce White, 2016, F. A. Davis Company). Typical ranges of arm movements relative to the neural arm position include flexion, extension, abduction, adduction. One of the patient's arm movements that caused the maximum pain was selected. The degree of the patient's movement restrictions and the associated pain for each movement restriction were quantified according to the standard guidelines thoroughly.
5. The patient's arm muscle trigger point and area of joint restriction was located following these steps: 1) First the patient's arm muscle causing pain and limiting the movements was determined. 2) Then the center of arm muscle belly causing the pain was found and pressed transversely to the fibers to assess the tenderness, stiffness, pliability, and any transient asynchronous muscle contractions. At the trigger point, the tissue is generally tender and elicits pain when touched. The muscles may also have transient asynchronous contractions at the resting state. 3) An area of a joint restriction was located by passively moving patient's joint to and away from the restriction and placing fingertips over a muscle were a that did not move.
6. A suitable size and shape dome (3.5 in or 4.5 in inner diameter dome with a curved edge bottom) was chosen to cover an approximate area of an identified trigger point and the joint restriction causing the pain at patient's dorsal site of the hand as the patients extended right arm fully.
7. The dome was placed over the trigger point and joint restriction on the patient's right hand while patient's arm in a position where the patient feels the maximum pain. And a predetermined subatmospheric pressure was applied to the dome using a vacuum pump sealingly connected to the dome through a vacuum manifold as disclosed herein and maintained for a preselected time interval, usually 15-60 seconds.
8. The patient was asked to straighten the fingers on a flat surface as much as possible then hold this position for 3 seconds. The active stretching of the patient's right hand in combination with the tissue reconfiguration therapy using domes at step 7 were repeated three times.
9. The dome was released from the patient's hand and upper back by lifting the check valve on the top of the dome and allowing air into the dome and repositioned near the previously dome ped were a including the trigger point. Steps 7 to 9 were repeated till all the trigger point area was covered.
10. A suitable size dome was placed over the trigger point on ventral side of patient's lower right arm while patient's arm in a position where the patient feels the maximum pain. And a predetermined subatmospheric pressure was applied to the dome using a vacuum pump sealingly connected to the dome through a vacuum manifold as disclosed herein and maintained for a preselected time interval, usually 15-60 seconds.
11. The patient was asked to hold the affected arm in fully extended position, hold this position for 3 seconds, and relax during the tissue reconfiguration therapy using domes. This active stretching exercises of the affected arm in combination with the tissue reconfiguration therapy using domes at step 11 were repeated three times.
12. The dome was released from the lower arm by lifting the check valve on the top of the dome and allowing air into the dome and repositioned near the previously dome ped were a including the trigger point. Steps 10 to 12 were repeated till the trigger point area was covered.
13. A suitable size dome was placed on the patient's affected arm on long head bicep brachii muscle while patient's arm in a position where the patient feels the maximum pain. And a predetermined subatmospheric pressure was applied to the dome using a vacuum pump sealingly connected to the dome through a vacuum manifold as disclosed herein and maintained for a preselected time interval, usually 15-60 seconds.
14. The patient was asked to extend arm fully, hold this position for 3 seconds, and relax during the tissue reconfiguration therapy using domes. This active stretching exercises of the affected arm in combination with the tissue reconfiguration therapy using domes at step 14 were repeated three times.
15. The dome was released from the patient's long head biceps muscle by lifting the check valve on the top of the dome and allowing air into the dome.
16. A suitable size dome was placed the patient's affected arm on short head bicep brachii muscle while the patient's arm in a position where the patient feels the maximum pain. And a predetermined subatmospheric pressure was applied to the dome using a vacuum pump sealingly connected to the dome through a vacuum manifold as disclosed herein and maintained for a preselected time interval, usually 15-60 seconds.
17. The patient was asked to extend arm fully, hold this position for 3 seconds, and relax during the tissue reconfiguration therapy using domes. This active stretching exercises of the affected arm in combination with the tissue reconfiguration therapy using domes at step 14 were repeated three times.
18. The dome was released from the patient's short head biceps muscle by lifting the check valve on the top of the dome and allowing air into the dome.
19. The tenderness, stiffness, any muscle contractions at the patient's upper, lower arm, and hand tissue at resting state were re-examined after the therapy and compared with the measurements at the beginning of the therapy session.

20. The pain level of the patient was re-assessed to monitor the effect of the tissue reconfiguration therapy using domes in combination with stretching exercise.
21. A suitable size dome was placed over the patient's lower arm near the affected wrist while patient's wrist bended position where the patient felt the maximum pain. And a predetermined subatmospheric pressure was applied to the dome using a vacuum pump sealingly connected to the dome through a vacuum manifold as disclosed herein and maintained for a preselected time interval, usually 15-60 seconds.
22. The therapist or the patient bent the affected arm and held this position for 3 seconds, and relaxed during the tissue reconfiguration therapy using domes. This active and passive stretching exercises of the affected wrist in combination with the tissue reconfiguration therapy using domes at step 25 were repeated three times.
23. The dome was released from the patient's lower arm by lifting the check valve on the top of the dome and allowing air into the dome and repositioned on proximally to previously manipulated tissue region using domes in a slightly overlapping manner to covered soft tissue regions on the lower arm found to be stiff.
24. The patient has also wrist movement restrictions that causes pain, particularly wrist extension.
25. A dome (4.5 in inner diameter with curved edge bottom) was placed over the trigger point on ventral intrinsic muscle of patient's hand while patient's wrist in a position that made the patient feel maximum pain. And a predetermined subatmospheric pressure was applied to the dome using a vacuum pump sealingly connected to the dome through a vacuum manifold as disclosed herein and maintained for a preselected time interval, usually 15-60 seconds.
24. The patient was asked to curl the finger on the affected hand, hold this position for 3 second, straighten the fingers and relax while the tissue reconfiguration therapy using domes. This active stretching exercises of the fingers in combination with the tissue reconfiguration therapy using domes at step 21 were repeated three times.
25. The dome was released from the ventral intrinsic muscle of the patient's hand by lifting the check valve on the top of the dome and allowing air into the dome.
26. The tenderness and stiffness of the patient's affected wrist tissue at resting state were re-examined after the therapy and compared with the measurements at the beginning of the therapy session.
27. The end ranges of patient's specific wrist movements were re-measured to monitor the effect of the tissue reconfiguration therapy using domes in combination with stretching exercises and the massage therapy.

In the foregoing specification, various aspects are described with reference to specific embodiments, but those skilled in the art will recognize that further aspects are not limited thereto. Various features and aspects described above may be used individually or jointly. Other aspects of the disclosure, including alternatives, modifications, permutations and equivalents of the embodiments described herein, will be apparent to those skilled in the art from consideration of the specification, study of the drawings, and practice of the various aspects. Further, various aspects can be utilized in any number of environments and applications beyond those described herein without departing from the broader spirit and scope of the description. The written description and accompanying drawings are, accordingly, to be regarded as illustrative rather than restrictive.

What is claimed is:

1. A method of treating at least one of an impaired movement and pain of a patient, the method comprising:

determining at least one trigger point location associated with the impaired movement and the pain, selecting an area of skin covering the trigger point location, placing a base of a dome in sealable contact with skin surrounding the selected area of skin covering the trigger point location, evacuating the dome to a first preselected value of pressure through a gas passage, whereby the first preselected value of pressure is applied to the area of skin, maintaining the first preselected value of pressure for a first preselected time interval;

increasing a value of pressure in the dome from the first preselected value of pressure to a second preselected value of pressure at the end of the first selected time interval, and maintaining the second preselected value of pressure in the dome for a second preselected time interval;

applying an electrical stimulation having preselected values of intensity, frequency, and waveform to the selected skin area enclosed by the dome during a third preselected time interval;

terminating electrical stimulation of the selected skin area at the end of the third selected time interval;

monotonically increasing the value of pressure in the dome from the second preselected value of pressure to an ambient pressure;

providing a photodetector configured to sense radiation operable to detect a preselected distance of skin tissue extruded into the dome, wherein the radiation comprises at least one of visible light and infrared radiation;

sensing the radiation with the photodetector;

detecting a change in an extruded distance of the skin tissue based on the sensing of the radiation; and selecting an end of the time of the first time interval for maintaining the preselected value of subatmospheric pressure based on the detection of the change in the extruded distance of the skin tissue;

wherein the electrical stimulus is applied to the selected skin area through two or more electrodes positioned on the base of the dome or inside the dome.

* * * * *